(12) United States Patent
Saroha et al.

(10) Patent No.: US 11,497,470 B2
(45) Date of Patent: Nov. 15, 2022

(54) FLEXIBLE PHASED ARRAY TRANSDUCER FOR INTRAVASCULAR IMAGING DEVICE AND ASSOCIATED DEVICES, SYSTEMS, AND METHODS

(71) Applicant: KONINKLIJKE PHILIPS N.V., Eindhoven (NL)

(72) Inventors: Princeton Saroha, Ladera Ranch, CA (US); Maritess Minas, San Diego, CA (US); David Kenneth Wrolstad, Fallbrook, CA (US); Jeremy Stigall, Carlsbad, CA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 811 days.

(21) Appl. No.: 16/336,352

(22) PCT Filed: Sep. 25, 2017

(86) PCT No.: PCT/EP2017/074158
§ 371 (c)(1),
(2) Date: Mar. 25, 2019

(87) PCT Pub. No.: WO2018/060109
PCT Pub. Date: Apr. 5, 2018

(65) Prior Publication Data
US 2019/0216426 A1     Jul. 18, 2019

Related U.S. Application Data

(60) Provisional application No. 62/401,409, filed on Sep. 29, 2016.

(51) Int. Cl.
*A61B 8/12* (2006.01)
*A61B 8/00* (2006.01)
(Continued)

(52) U.S. Cl.
CPC ............... *A61B 8/445* (2013.01); *A61B 8/12* (2013.01); *A61B 8/4488* (2013.01);
(Continued)

(58) Field of Classification Search
CPC ......... A61B 8/12; A61B 8/445; A61B 8/4488; A61B 8/4494; B06B 1/0622;
(Continued)

(56) References Cited

U.S. PATENT DOCUMENTS 5,359,760 A    11/1994  Busse
5,539,965 A     7/1996  Safari
(Continued)

FOREIGN PATENT DOCUMENTS

JP        2013099 A     1/1990
JP       10315472 A    12/1998
JP      H11274592 A    10/1999

*Primary Examiner* — Mark D Remaly

(57) ABSTRACT

A method for fabricating an intravascular imaging assembly is provided. In one embodiment, the method includes forming a stacked structure (415) having a plurality of sacrificial material layers disposed between a plurality of ultrasound material layers in an alternating pattern; dicing the stacked structure (420) to form a plurality of elongated strips, each comprising an array of ultrasound elements defined by the plurality of ultrasound material layers and spacers defined by the plurality of sacrificial material layers; coupling a first elongated strip (430) of the plurality of elongated strips to a flexible circuit substrate; and removing the spacers (435) of the first elongated strip from the flexible circuit substrate.

7 Claims, 39 Drawing Sheets

(51) Int. Cl.
*B06B 1/06* (2006.01)
*H01L 41/047* (2006.01)
*H01L 41/29* (2013.01)
*H01L 41/338* (2013.01)

(52) U.S. Cl.
CPC .......... *A61B 8/4494* (2013.01); *B06B 1/0622* (2013.01); *B06B 1/0633* (2013.01); *H01L 41/0475* (2013.01); *H01L 41/29* (2013.01); *H01L 41/338* (2013.01); *B06B 2201/76* (2013.01)

(58) Field of Classification Search
CPC .............. B06B 1/0633; B06B 2201/76; H01L 41/0475; H01L 41/29; H01L 41/338
See application file for complete search history.

(56) References Cited

U.S. PATENT DOCUMENTS

| | | | |
|---|---|---|---|
| 6,183,578 B1 | 2/2001 | Ritter | |
| 7,226,417 B1 * | 6/2007 | Eberle | ................... B06B 1/0633 29/25.35 |
| 2002/0130590 A1 | 9/2002 | Shiraishi | |
| 2007/0239024 A1 | 10/2007 | Eberle et al. | |
| 2008/0160324 A1 | 7/2008 | Ohmori et al. | |
| 2015/0305716 A1 | 10/2015 | Rice et al. | |

* cited by examiner

FLEXIBLE PHASED ARRAY TRANSDUCER FOR INTRAVASCULAR IMAGING DEVICE AND ASSOCIATED DEVICES, SYSTEMS, AND METHODS

This application is the U.S. National Phase application under 35 U.S.C. § 371 of International Application No. PCT/EP2017/074158, filed on Sep. 25, 2017, which claims the benefit of Provisional Application Ser. No. 62/401,409, filed Sep. 29, 2016. These applications are hereby incorporated by reference herein.

TECHNICAL FIELD

The present disclosure relates generally to intravascular ultrasound (IVUS) imaging and, in particular, to the intravascular imaging assembly of a solid-state IVUS imaging device. For example, the intravascular imaging assembly can include phased array transducers positioned circumferentially around a support structure. The fabrication of the phased array transducers can be designed to facilitate creation of high-resolution, high-quality images and to allow for large-volume, high-yield production.

BACKGROUND

Intravascular ultrasound (IVUS) imaging is widely used in interventional cardiology as a diagnostic tool for assessing a diseased vessel, such as an artery, within the human body to determine the need for treatment, to guide the intervention, and/or to assess its effectiveness. An IVUS device including one or more ultrasound transducers is passed into the vessel and guided to the area to be imaged. The transducers emit ultrasonic energy in order to create an image of the vessel of interest. Ultrasonic waves are partially reflected by discontinuities arising from tissue structures (such as the various layers of the vessel wall), red blood cells, and other features of interest. Echoes from the reflected waves are received by the transducer and passed along to an IVUS imaging system. The imaging system processes the received ultrasound echoes to produce a cross-sectional image of the vessel where the device is placed.

There are two types of IVUS catheters commonly in use today: rotational and solid-state. For a typical rotational IVUS catheter, a single ultrasound transducer element is located at the tip of a flexible driveshaft that spins inside a plastic sheath inserted into the vessel of interest. The transducer element is oriented such that the ultrasound beam propagates generally perpendicular to the axis of the device. The fluid-filled sheath protects the vessel tissue from the spinning transducer and driveshaft while permitting ultrasound signals to propagate from the transducer into the tissue and back. As the driveshaft rotates, the transducer is periodically excited with a high voltage pulse to emit a short burst of ultrasound. The same transducer then listens for the returning echoes reflected from various tissue structures. The IVUS imaging system assembles a two dimensional display of the vessel cross-section from a sequence of pulse/acquisition cycles occurring during a single revolution of the transducer.

Solid-state IVUS catheters carry a sensing assembly or scanner assembly that includes an array of ultrasound transducers distributed around its circumference along with one or more integrated circuit controller chips mounted adjacent to the transducer array. The solid-state IVUS catheters are also referred to as phased array IVUS transducers or phased array IVUS devices. The controllers select individual transducer elements (or groups of elements) for transmitting an ultrasound pulse and for receiving the ultrasound echo signal. By stepping through a sequence of transmit-receive pairs, the solid-state IVUS system can synthesize the effect of a mechanically scanned ultrasound transducer but without moving parts (hence the solid-state designation). Since there is no rotating mechanical element, the transducer array can be placed in direct contact with the blood and vessel tissue with minimal risk of vessel trauma. Furthermore, because there is no rotating element, the electrical interface is simplified. The solid-state scanner can be wired directly to the imaging system with a simple electrical cable and a standard detachable electrical connector, rather than the complex rotating electrical interface required for a rotational IVUS device.

Manufacturing an intravascular imaging device that can efficiently traverse physiology within the human body and effectively create high-resolution, high-quality vascular images is challenging. For example, some phased array IVUS devices can have a maximum of about 32 or 64 transducers in a transducer array due to the sizes and the manufacturing of the phased array IVUS devices. As such, images created from phased array IVUS devices may have limited resolution and/or limited quality. Therefore, while conventional methods of forming phased array IVUS devices are generally adequate for their intended purposes, they have not been entirely satisfactory in every aspect.

SUMMARY

Embodiments of the present disclosure provide improved phased array transducers for use in intravascular ultrasound (IVUS) imaging. The phased array transducers can be used in a flat configuration or a rolled configuration with suitable support structures. The phased array transducers can be fabricated by leveraging semiconductor fabrication techniques such as layer deposition and sputter deposition to precisely control the dimensions and placements of transducers in the transducer arrays. As such, transduce arrays can be produced with a greater number of smaller size transducers and the transducers can be more uniform in size and more uniformly distributed than using conventional techniques. Thus, the disclosed embodiments can improve image resolution and quality.

In one embodiment, a method for fabricating an intravascular imaging assembly is provided. The method includes forming a stacked structure having a plurality of sacrificial material layers disposed between a plurality of ultrasound material layers in an alternating pattern; dicing the stacked structure to form a plurality of elongated strips, each comprising an array of ultrasound elements defined by the plurality of ultrasound material layers and spacers defined by the plurality of sacrificial material layers; coupling a first elongated strip of the plurality of elongated strips to a flexible circuit substrate; and removing the spacers of the first elongated strip from the flexible circuit substrate.

In some embodiments, the forming the stacked structure includes forming at least 32 ultrasound material layers. In some embodiments, each of the plurality of sacrificial material layers has a thickness between 0.01 micrometers (μm) and 125 μm. In some embodiments, each of the plurality of ultrasound material layers has a thickness between 5 micrometers (μm) and 125 μm. In some embodiments, the plurality of sacrificial material layers comprise a material from a group of sacrificial materials consisting of: silicon oxides, silicon dioxides, aluminum, chromium, phosphosilicate glass, or borophosphosilicate glass. In some embodiments, the plurality of ultrasound material layers comprise a material from a group of ultrasound materials consisting of: piezoelectric zirconate transducers (PZT), polyvinylidene difluoride (PVDF), or PZT-PVDF composite. In some embodiments, the dicing the stacked structure includes dicing the stacked structure along a first plane. In some embodiments, the dicing the stacked structure includes dicing the stacked structure along a second plane perpendicular to the first plane. In some embodiments, the method includes forming an additional sacrificial layer over the stacked structure along the first plane after the dicing. In some embodiments, the removing the spacers of the first elongated strip from the flexible circuit substrate includes etching away the plurality of sacrificial material layers defining the spacers. In some embodiments, the method includes forming a combined strip having by a post sacrificial material layer holding the first elongated strip and a second elongated strip of the plurality of elongated strips together; coupling the combined strip to the flexible circuit substrate such that the first elongated strip and the second elongated strip are coupled to the flexible circuit substrate; and removing the post sacrificial material layer of the combined strip and the spacers of the second elongated strip from the flexible circuit substrate. In some embodiments, the forming the combined strip includes positioning the first elongated strip and the second elongated strip such that the array of ultrasound elements of the first elongated strip are aligned with the array of ultrasound elements of the second elongated strip prior to depositing the post sacrificial material layer. In some embodiments, the forming the combined strip includes positioning the first elongated strip and the second elongated strip such that the array of ultrasound elements of the first elongated strip are offset with the array of ultrasound elements of the second elongated strip. In some embodiments, the method includes wrapping the flexible circuit substrate around a support member; fixedly securing the flexible circuit substrate to the support member; and coupling the support member to a distal portion of an intravascular device.

In one embodiment, a method for fabricating an intravascular imaging assembly is provided. The method includes forming a plurality of recesses in a substrate formed of a sacrificial material; filling at least a portion of the plurality of recesses in the substrate with an ultrasound material; dicing the substrate to form an elongated strip comprising an array of ultrasound elements defined by the ultrasound material and spacers defined by the sacrificial material; coupling the elongated strip to a flexible circuit substrate; and removing the spacers of the elongated strip from the flexible circuit substrate.

In some embodiments, the dicing the substrate includes dicing the substrate such that the elongated strip includes a first array of ultrasound elements spaced from a second array of ultrasound elements. In some embodiments, the ultrasound elements of the first array of ultrasound elements are aligned with the ultrasound elements of the second array of ultrasound elements. In some embodiments, the forming the plurality of recesses in the substrate includes forming a first series of recesses aligned with a second series of recesses. In some embodiments, the ultrasound elements of the first array of ultrasound elements are offset with respect to the ultrasound elements of the second array of ultrasound elements. In some embodiments, the forming the plurality of recesses in the substrate includes forming a first series of recesses offset with respect to a second series of recesses. In some embodiments, the removing the spacers of the elongated strip from the flexible circuit substrate includes etching away the sacrificial material defining the spacers. In some embodiments, the method includes wrapping the flexible circuit substrate around a support member; fixedly securing the flexible circuit substrate to the support member; and coupling the support member to a distal portion of an intravascular device.

In one embodiment, an intravascular imaging device is provided. The intravascular imaging device includes a flexible elongate member having a proximal portion and a distal portion; and an intravascular imaging assembly coupled to the distal portion of the flexible elongate member, the intravascular imaging assembly comprising a flexible circuit; and an ultrasound transducer array disposed on the flexible circuit, wherein the ultrasound transducer array includes a plurality of ultrasound elements spaced apart by a pitch width less than 10 micrometers (µm) to facilitate creation of an intravascular image of a minimum predetermined signal resolution.

In some embodiments, the ultrasound transducer array consists of a single array. In some embodiments, the ultrasound transducer array comprises of a first array of ultrasound elements spaced from a second array of ultrasound elements. In some embodiments, the ultrasound elements of the first array of ultrasound elements are aligned with the ultrasound elements of the second array of ultrasound elements. In some embodiments, the ultrasound elements of the first array of ultrasound elements are offset with respect to the ultrasound elements of the second array of ultrasound elements. In some embodiments, the pitch width between the plurality of ultrasound elements is defined by removal of a sacrificial material positioned between the plurality of ultrasound elements.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which.

DETAILED DESCRIPTION

Figure 1:
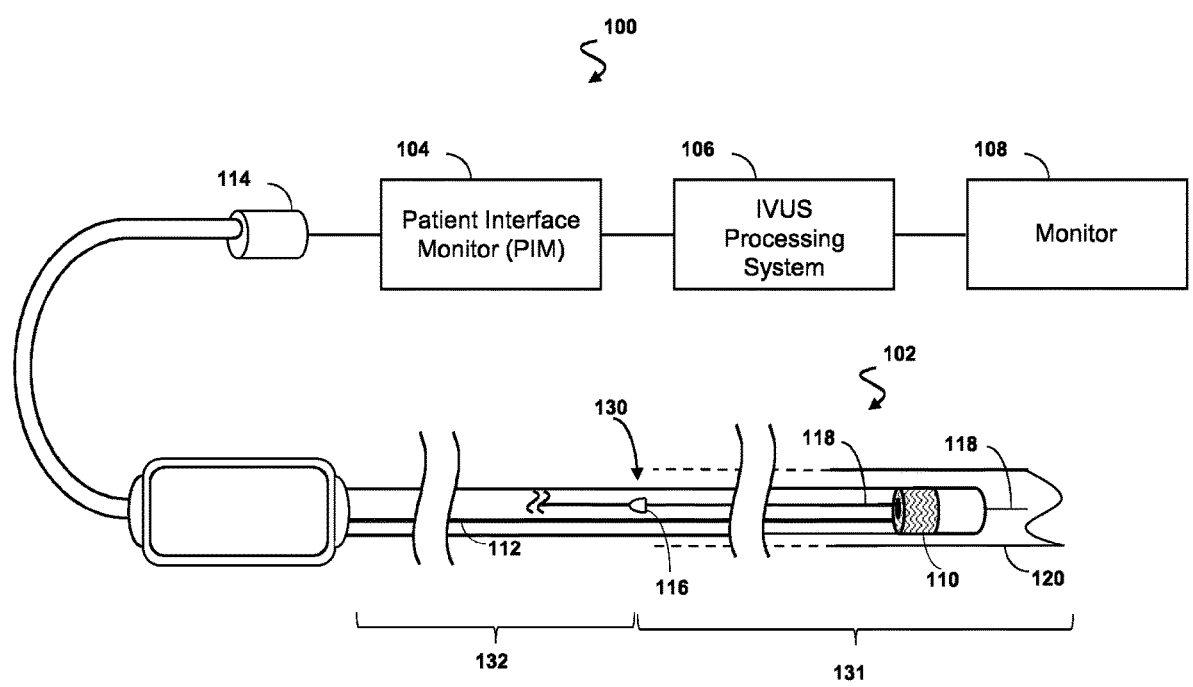
FIG. 1 is a diagrammatic schematic view of an intravascular ultrasound (IVUS) imaging system, according to aspects of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

In most phased array IVUS device, there is a compromise between usability, image quality, image resolution, and stiff length. One approach to improving image resolution and/or quality is to add more ultrasound transducers or elements. However, the stiff length of the phased array IVUS device also increases. Thus, it may be difficult for a physician to maneuver the phased array IVUS device through small tortuous anatomical pathways. In addition, the sizes or profiles of phased array IVUS transducer devices are commonly greater than rotational IVUS device. As such, adding more ultrasound elements may further increase the size or profile, and thus may not be desirable. Another approach is to reduce the size of each individual ultrasound element so that a greater number of ultrasound elements may be fitted without increasing the size of the phased array IVUS device. For a transducer array with 64 or more ultrasound elements, each ultrasound element may be in an order of 100 micrometer (μm). The small footprint can be problematic for fabrication. For example, some fabrication methods include dicing a sheet or a strip of ultrasound transducer material into individual ultrasound elements and bonding the individual ultrasound elements onto a flex circuit to form a transducer array. Some other fabrication methods include forming a sheet of ultrasound transducer material on a flex circuit and dicing the sheet to form an array of ultrasound elements. The dicing of the smaller size ultrasound elements can cause cracks and/or fractures, and thus may impact yield performance. In addition, aligning smaller size ultrasound elements during the bonding may be difficult.

Disclosed herein are various embodiments of providing an improved phased array IVUS device. For example, a distal portion of a phased array IVUS device can include a transducer array disposed on a flex circuit arranged in a cylindrical shape. The transducer array can include 32, 64, 128, or more ultrasound transducers with identical dimensions uniformly spaced on the flexible circuit. The disclosed embodiments provide methods of fabricating the transducer array. In one embodiment, the fabrication method includes forming a stacked structure with alternating layers of sacrificial material and ultrasound material, dicing the stacked structure to form an elongated strip. The elongated strip includes an array of ultrasound elements separated by spacers. The ultrasound material layers define the ultrasound elements. The sacrificial material layers define the spacers. The fabrication method further includes coupling the elongated strip to a flex circuit and removing the spacers from the flex circuit. In another embodiment, the fabrication method includes forming recesses in a substrate of a sacrificial material, filling the recesses with an ultrasound material, and dicing the ultrasound material filled substrate to form an elongated strip. The recesses can be formed in any suitable pattern such as in alignment or offset to create images of desirable resolution and/or vasculature view. The disclosed embodiments can provide images with improved image resolution and quality. The disclosed embodiments can allow for large-volume, high-yield production of phased array IVUS transducers. Although the disclosed embodiments are described in the context of phased array IVUS transducers, the disclosed embodiments are suitable for use in any type of piezoelectric zirconate transducers (PZT) technology-based device.

FIG. 1 is a diagrammatic schematic view of an IVUS imaging system 100, according to aspects of the present disclosure. The system 100 may include an IVUS device 102 such as a catheter such as a catheter, guide wire, or guide catheter, a patient interface module (PIM) 104, an IVUS processing system 106, such as a console and/or a computer, and a monitor 108.

The IVUS device 102 may include a scanner assembly 110 mounted at a distal portion 131 near a distal end of the IVUS device 102. At a high level, the IVUS device 102 emits ultrasonic energy from a transducer array included in scanner assembly 110. The ultrasonic energy is reflected by tissue structures in the medium, such as a vessel 120, surrounding the scanner assembly 110, and the ultrasound echo signals are received by the transducer array in the scanner assembly 110. The PIM 104 transfers the received echo signals to the IVUS processing system 106 where the ultrasound image (including the flow information) is reconstructed and displayed on the monitor 108. The IVUS processing system 106 can include a processor and a memory. The IVUS processing system 106 can be operable to facilitate the features of the system 100 described herein. For example, the processor can execute computer readable instructions stored on the non-transitory tangible computer readable medium.

Although the IVUS device 102 is described in the context of IVUS imaging, the IVUS device 102 can include any suitable type of physiologic sensing assembly configured to obtain physiologic data associated with pressure, flow, temperature, forward looking IVUS (FL-IVUS), intravascular photoacoustic (IVPA) imaging, a fractional flow reserve (FFR) determination, a functional measurement determination, a coronary flow reserve (CFR) determination, optical coherence tomography (OCT), computed tomography, intracardiac echocardiography (ICE), forward-looking ICE (FLICE), intravascular palpography, transesophageal ultrasound, and/or other suitable types of physiologic data.

The PIM 104 facilitates communication of signals between the IVUS processing system 106 and the scanner assembly 110 included in the IVUS device 102. This communication includes the steps of: (1) providing commands to integrated circuit controller chip(s) 206A, 206B, illustrated in FIG. 2, included in the scanner assembly 110 to select the particular transducer array element(s) to be used for transmit and receive, (2) providing the transmit trigger signals to the integrated circuit controller chip(s) 206A, 206B included in the scanner assembly 110 to activate the transmitter circuitry to generate an electrical pulse to excite the selected transducer array element(s), and/or (3) accepting amplified echo signals received from the selected transducer array element(s) via amplifiers included on the integrated circuit controller chip(s) 206 of the scanner assembly 110. In some embodiments, the PIM 104 performs preliminary processing of the echo data prior to relaying the data to the IVUS processing system 106. In examples of such embodiments, the PIM 104 performs amplification, filtering, and/or aggregating of the data. In an embodiment, the PIM 104 also supplies high- and low-voltage direct current (DC) power to support operation of the device 102 including circuitry within the scanner assembly 110.

The IVUS processing system 106 receives the echo data from the scanner assembly 110 by way of the PIM 104 and processes the data to reconstruct an image of the tissue structures in the medium surrounding the scanner assembly 110. The IVUS processing system 106 outputs image data such that an image of a vessel, such as a cross-sectional image of the vessel 120, is displayed on the monitor 108. The vessel 120 may represent fluid filled or surrounded structures, both natural and man-made. The vessel 120 may be within a body of a patient. The vessel 120 may be a blood vessel, as an artery or a vein of a patient's vascular system, including cardiac vasculature, peripheral vasculature, neural vasculature, renal vasculature, and/or or any other suitable lumen inside the body. For example, the IVUS device 102 may be used to examine any number of anatomical locations and tissue types, including without limitation, organs including the liver, heart, kidneys, gall bladder, pancreas, lungs; ducts; intestines; nervous system structures including the brain, dural sac, spinal cord and peripheral nerves; the urinary tract; as well as valves within the blood, chambers or other parts of the heart, and/or other systems of the body. In addition to natural structures, the IVUS device 102 may be used to examine man-made structures such as, but without limitation, heart valves, stents, shunts, filters and other devices.

Figure 2:
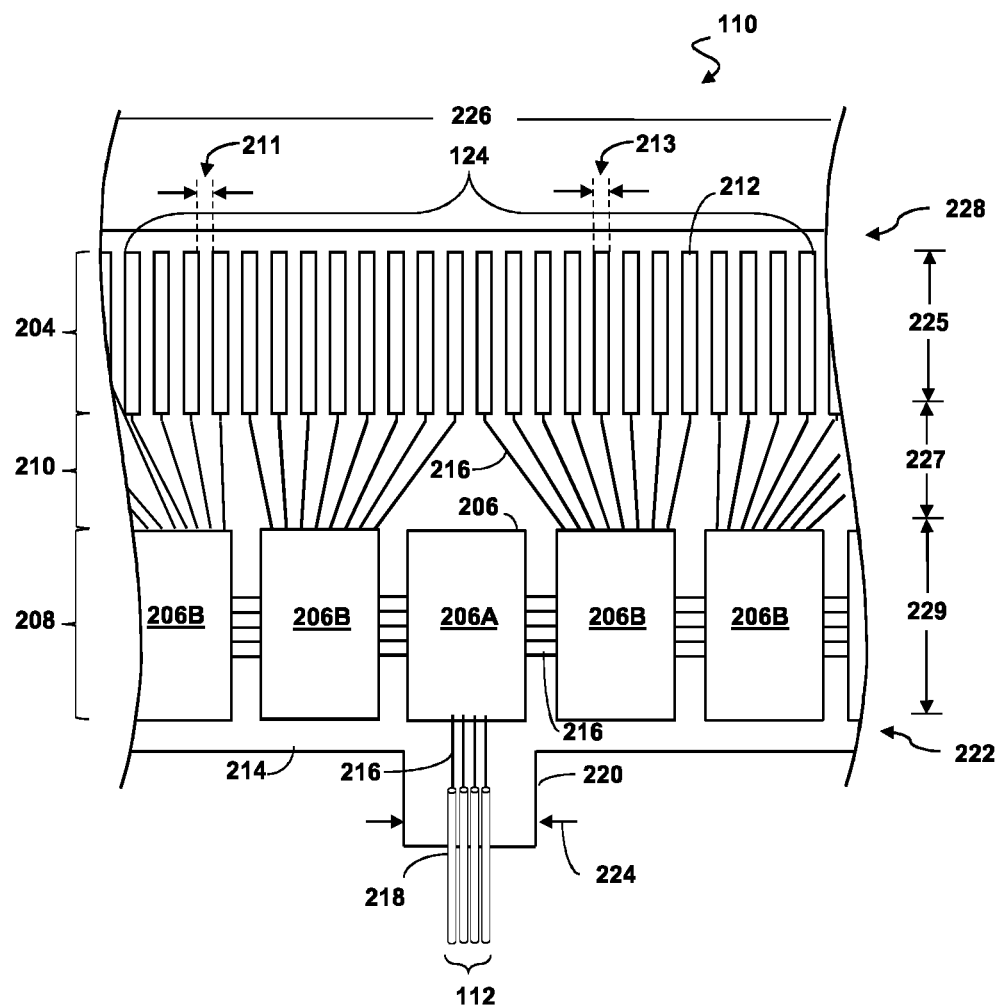
FIG. 2 is a diagrammatic top view of a portion of IVUS imaging assembly in a flat configuration, according to aspects of the present disclosure.

In some embodiments, the IVUS device 102 includes some features similar to traditional solid-state IVUS catheters, such as the EagleEye® catheter available from Volcano Corporation and those disclosed in U.S. Pat. No. 7,846,101 hereby incorporated by reference in its entirety. For example, the IVUS device 102 includes the scanner assembly 110 near a distal end of the IVUS device 102 and an electrical cable 112 extending along the longitudinal body of the IVUS device 102. The cable 112 is a transmission line bundle including a plurality of conductors, including one, two, three, four, five, six, seven, or more conductors 218 (FIG. 2). It is understood that any suitable gauge wire can be used for the conductors 218. In an embodiment, the cable 112 can include a four-conductor transmission line arrangement with, e.g., 41 American wire gauge (AWG) wires. In an embodiment, the cable 112 can include a seven-conductor transmission line arrangement utilizing, e.g., 44 AWG wires. In some embodiments, 43 AWG wires can be used.

The cable 112 terminates in a PIM connector 114 at a proximal end of the IVUS device 102. The PIM connector 114 electrically couples the cable 112 to the PIM 104 and physically couples the IVUS device 102 to the PIM 104. In an embodiment, the IVUS device 102 further includes a guide wire exit port 116 disposed near a junction 130 at which a distal portion 131 is coupled to a proximal portion 132. Accordingly, in some instances the IVUS device 102 is a rapid-exchange catheter. The guide wire exit port 116 allows a guide wire 118 to be inserted towards the distal end in order to direct the IVUS device 102 through the vessel 120.

Figure 3:
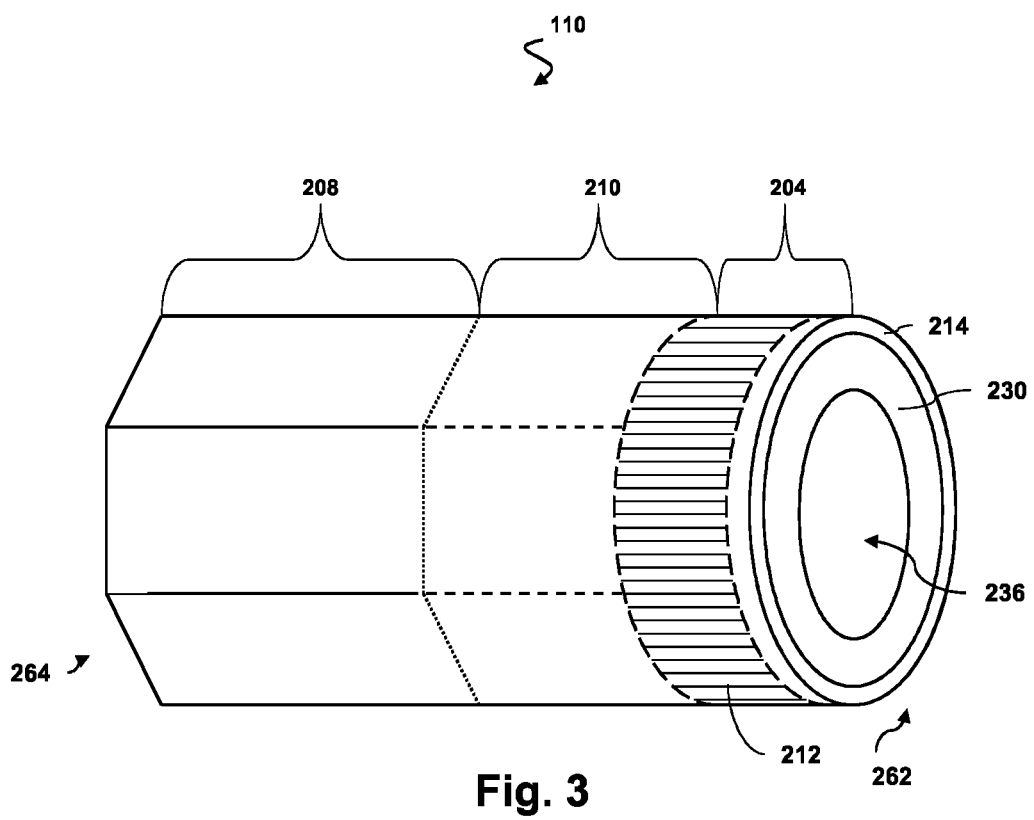
FIG. 3 is a diagrammatic side view of IVUS imaging assembly, including a flex circuit in a rolled configuration around a support member, according to aspects of the present disclosure.

FIG. 2 is a diagrammatic top view of a portion of a scanner assembly 110, according to aspects of the present disclosure. The scanner assembly 110 includes a transducer array 124 formed in a transducer region 204 and transducer control logic dies 206 (including dies 206A and 206B) formed in a control region 208, with a transition region 210 disposed therebetween. The transducer array 124 includes an array of IVUS transducers 212. The transducer control logic dies 206 and the transducers 212 are mounted on a flex circuit 214 that is shown in a flat configuration in FIG. 2. Although the scanner assembly 110 shown in FIG. 2 is an IVUS imaging assembly, it is understood that the scanner assembly 110 may be configured to obtain any type of physiologic data. FIG. 3 illustrates a rolled configuration of the flex circuit 214. The transducer array 124 is a non-limiting example of a medical sensor element and/or a medical sensor element array. The transducer control logic dies 206 is a non-limiting example of a control circuit. The transducer region 204 is disposed adjacent a distal portion 228 of the flex circuit 214. The control region 208 is disposed adjacent the proximal portion 222 of the flex circuit 214. The transition region 210 is disposed between the control region 208 and the transducer region 204. Dimensions of the transducer region 204, the control region 208, and the transition region 210 (e.g., lengths 225, 227, 229) can vary in different embodiments. In some embodiments, the lengths 225, 227, 229 can be substantially similar or a length 227 of the transition region 210 can be greater than lengths 225, 229 of the transducer region and controller region, respectively. While the scanner assembly 110 is described as including a flex circuit, it is understood that the transducers and/or controllers may be arranged to form the scanner assembly 110 in other configurations, including those omitting a flex circuit.

The transducer array 124 can include any number and type of ultrasound transducers 212 spaced apart by a pitch width 211, although for clarity only a limited number of ultrasound transducers are illustrated in FIG. 2. In an embodiment, the transducer array 124 includes 64 individual ultrasound transducers 212. In a further embodiment, the transducer array 124 includes 32 ultrasound transducers 212. Other numbers are both contemplated and provided for. With respect to the types of transducers, in an embodiment, the ultrasound transducers 212 are piezoelectric micromachined ultrasound transducers (PMUTs) fabricated on a microelectromechanical system (MEMS) substrate using a polymer piezoelectric material, for example as disclosed in U.S. Pat. No. 6,641,540, which is hereby incorporated by reference in its entirety. In alternate embodiments, the transducer array includes PZT transducers such as bulk PZT transducers, capacitive micromachined ultrasound transducers (cMUTs), single crystal piezoelectric materials, other suitable ultrasound transmitters and receivers, and/or combinations thereof. As described in greater detail herein, the fabrication of the transducer array 124 can leverage semiconductor manufacturing techniques to reduce the width 213 of the transducers 212 and the pitch width 211.

The scanner assembly 110 may include various transducer control logic, which in the illustrated embodiment is divided into discrete control logic dies 206. In various examples, the control logic of the scanner assembly 110 performs: decoding control signals sent by the PIM 104 across the cable 112, driving one or more transducers 212 to emit an ultrasonic signal, selecting one or more transducers 212 to receive a reflected echo of the ultrasonic signal, amplifying a signal representing the received echo, and/or transmitting the signal to the PIM across the cable 112. In the illustrated embodiment, a scanner assembly 110 having 64 ultrasound transducers 212 divides the control logic across nine control logic dies 206, of which five are shown in FIG. 2. Designs incorporating other numbers of control logic dies 206 including 8, 9, 16, 17 and more are utilized in other embodiments. In general, the control logic dies 206 are characterized by the number of transducers they are capable of driving, and exemplary control logic dies 206 drive 4, 8, and/or 16 transducers.

The control logic dies are not necessarily homogenous. In some embodiments, a single controller is designated a master control logic die 206A and contains the communication interface for the cable 112. Accordingly, the master control circuit may include control logic that decodes control signals received over the cable 112, transmits control responses over the cable 112, amplifies echo signals, and/or transmits the echo signals over the cable 112. The remaining controllers are slave controllers 206B. The slave controllers 206B may include control logic that drives a transducer 212 to emit an ultrasonic signal and selects a transducer 212 to receive an echo. In the depicted embodiment, the master controller 206A does not directly control any transducers 212. In other embodiments, the master controller 206A drives the same number of transducers 212 as the slave controllers 206B or drives a reduced set of transducers 212 as compared to the slave controllers 206B. In an exemplary embodiment, a single master controller 206A and eight slave controllers 206B are provided with eight transducers assigned to each slave controller 206B.

The flex circuit 214, on which the transducer control logic dies 206 and the transducers 212 are mounted, provides structural support and interconnects for electrical coupling. The flex circuit 214 may be constructed to include a film layer of a flexible polyimide material such as KAPTON™ (trademark of DuPont). Other suitable materials include polyester films, polyimide films, polyethylene napthalate films, or polyetherimide films, other flexible printed semiconductor substrates as well as products such as Upilex® (registered trademark of Ube Industries) and TEFLON® (registered trademark of E.I. du Pont). In the flat configuration illustrated in FIG. 2, the flex circuit 214 has a generally rectangular shape. As shown and described herein, the flex circuit 214 is configured to be wrapped around a support member 230 (FIG. 3) to form a cylindrical toroid in some instances. Therefore, the thickness of the film layer of the flex circuit 214 is generally related to the degree of curvature in the final assembled scanner assembly 110. In some embodiments, the film layer is between 5 μm and 100 μm, with some particular embodiments being between 12.7 μm and 25.1 μm.

To electrically interconnect the control logic dies 206 and the transducers 212, in an embodiment, the flex circuit 214 further includes conductive traces 216 formed on the film layer that carry signals between the control logic dies 206 and the transducers 212. In particular, the conductive traces 216 providing communication between the control logic dies 206 and the transducers 212 extend along the flex circuit 214 within the transition region 210. In some instances, the conductive traces 216 can also facilitate electrical communication between the master controller 206A and the slave controllers 206B. The conductive traces 216 can also provide a set of conductive pads that contact the conductors 218 of cable 112 when the conductors 218 of the cable 112 are mechanically and electrically coupled to the flex circuit 214. Suitable materials for the conductive traces 216 include copper, gold, aluminum, silver, tantalum, nickel, and tin, and may be deposited on the flex circuit 214 by processes such as sputtering, plating, and etching. In an embodiment, the flex circuit 214 includes a chromium adhesion layer. The width and thickness of the conductive traces 216 are selected to provide proper conductivity and resilience when the flex circuit 214 is rolled. In that regard, an exemplary range for the thickness of a conductive trace 216 and/or conductive pad is between 10-50 μm. For example, in an embodiment, 20 μm conductive traces 216 are separated by 20 μm of space. The width of a conductive trace 216 on the flex circuit 214 may be further determined by the width of the conductor 218 to be coupled to the trace/pad.

The flex circuit 214 can include a conductor interface 220 in some embodiments. The conductor interface 220 can be a location of the flex circuit 214 where the conductors 218 of the cable 112 are coupled to the flex circuit 214. For example, the bare conductors of the cable 112 are electrically coupled to the flex circuit 214 at the conductor interface 220. The conductor interface 220 can be tab extending from the main body of flex circuit 214. In that regard, the main body of the flex circuit 214 can refer collectively to the transducer region 204, controller region 208, and the transition region 210. In the illustrated embodiment, the conductor interface 220 extends from the proximal portion 222 of the flex circuit 214. In other embodiments, the conductor interface 220 is positioned at other parts of the flex circuit 214, such as the distal portion 228, or the flex circuit 214 omits the conductor interface 220. A value of a dimension of the tab or conductor interface 220, such as a width 224, can be less than the value of a dimension of the main body of the flex circuit 214, such as a width 226. In some embodiments, the substrate forming the conductor interface 220 is made of the same material(s) and/or is similarly flexible as the flex circuit 214. In other embodiments, the conductor interface 220 is made of different materials and/or is comparatively more rigid than the flex circuit 214. For example, the conductor interface 220 can be made of a plastic, thermoplastic, polymer, hard polymer, etc., including polyoxymethylene (e.g., DELRIN®), polyether ether ketone (PEEK), nylon, and/or other suitable materials.

In some instances, the scanner assembly 110 is transitioned from a flat configuration (FIG. 2) to a rolled or more cylindrical configuration (FIG. 3). For example, in some embodiments, techniques are utilized as disclosed in one or more of U.S. Pat. No. 6,776,763, titled "ULTRASONIC TRANSDUCER ARRAY AND METHOD OF MANUFACTURING THE SAME" and U.S. Pat. No. 7,226,417, titled "HIGH RESOLUTION INTRAVASCULAR ULTRASOUND SENSING ASSEMBLY HAVING A FLEXIBLE SUBSTRATE," each of which is hereby incorporated by reference in its entirety. FIG. 3 is a diagrammatic perspective view with the flex circuit 214 in the rolled configuration around the support member 230, according to aspects of the present disclosure. The support member 230 can be referenced as a unibody in some instances. The support member 230 can be composed of a metallic material, such as stainless steel, or non-metallic material, such as a plastic or polymer as described in U.S. Provisional Application No. 61/985, 220, "Pre-Doped Solid Substrate for Intravascular Devices," filed Apr. 28, 2014, ('220 application) the entirety of which is hereby incorporated by reference herein. The support member 230 can be a ferrule having a distal portion 262 and a proximal portion 264. The support member 230 can be a ferrule having a distal portion 262 and a proximal portion 264. The support member 230 can be tubular in shape and define a lumen 236 extending longitudinally therethrough. The lumen 236 can be sized and shaped to receive the guide wire 118. The support member 230 can be manufactured using any suitable process. For example, the support member 230 can be machined, such as by removing material from a blank to shape the support member 230, or molded, such as by an injection molding process.

Figure 4:
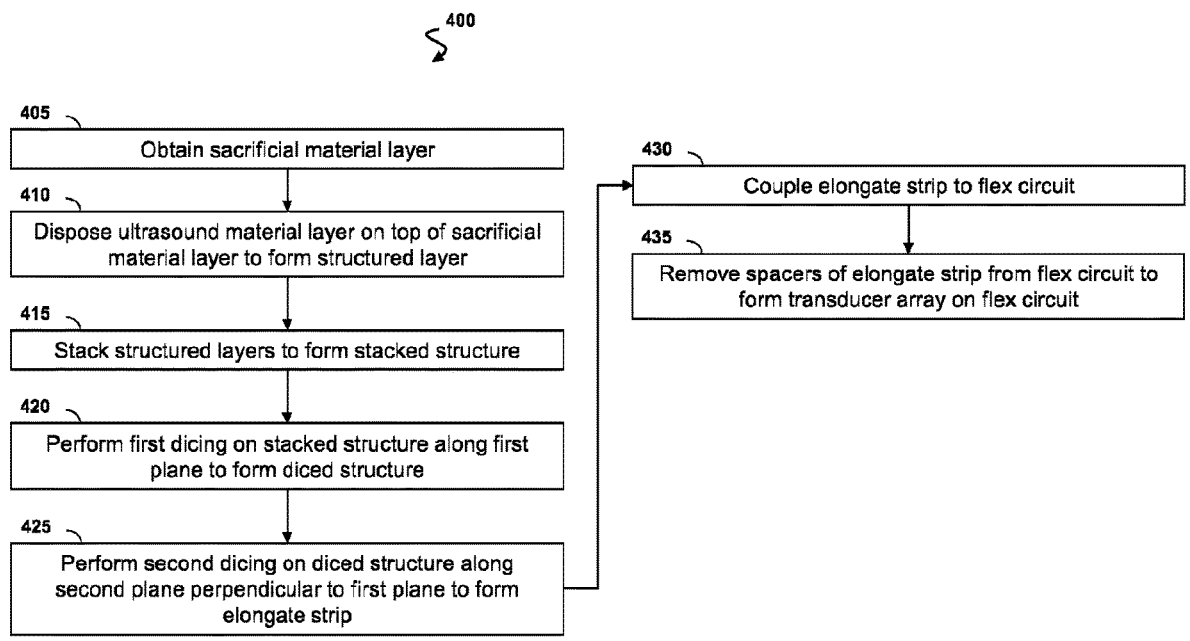
FIG. 4 is a flow diagram of a method of fabricating an intravascular imaging assembly, leveraging semiconductor manufacturing techniques described herein, according to aspects of the disclosure.
Figure 5A:
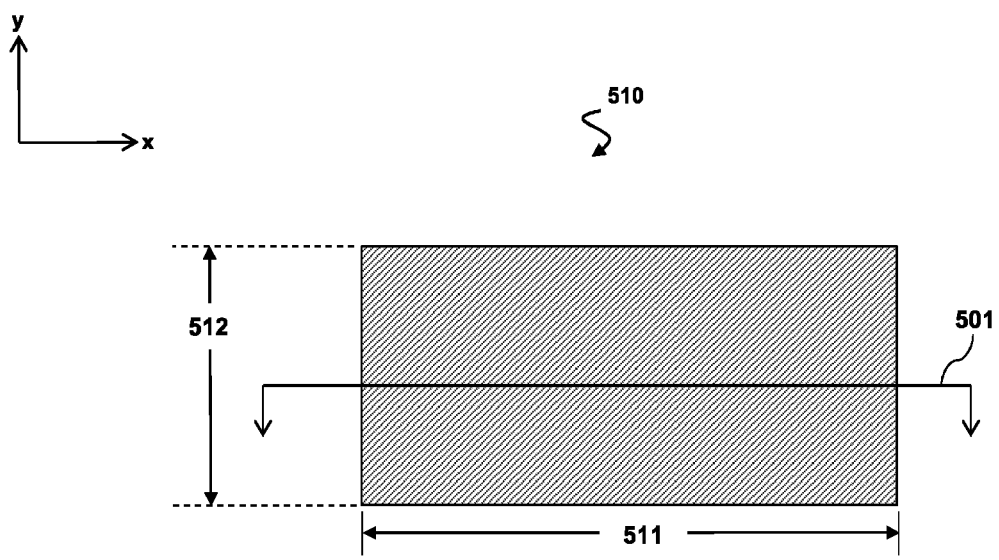
FIG. 5A is a diagrammatic top view of a sacrificial material layer in a stage of fabrication, according to aspects of the present disclosure.
Figure 5B:
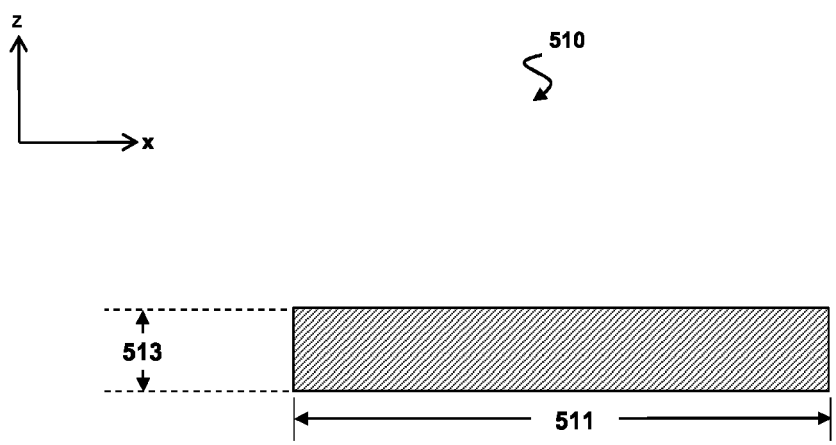
FIG. 5B is a diagrammatic cross-sectional view of a sacrificial material layer in a stage of fabrication, according to aspects of the present disclosure.
Figure 6A:
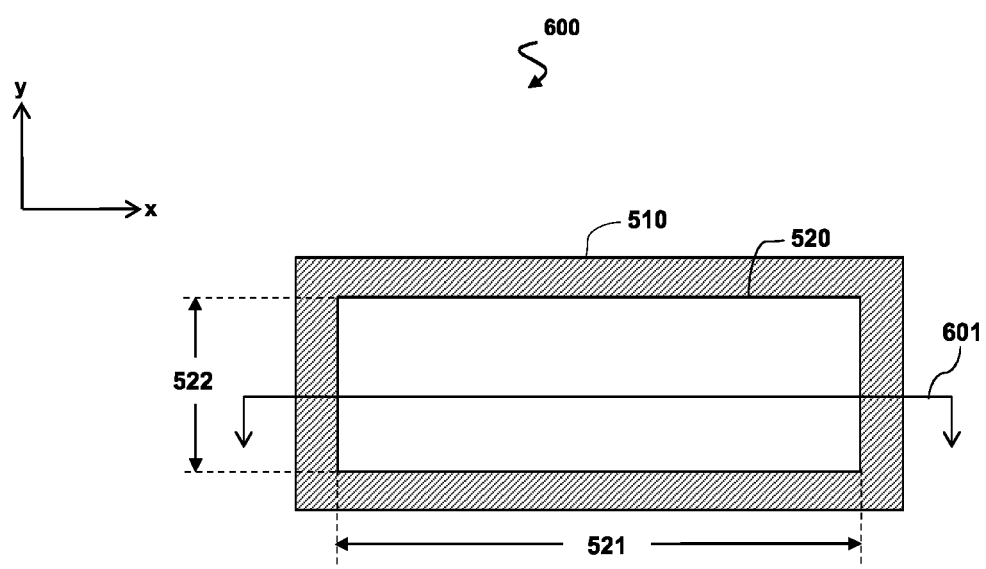
FIG. 6A is a diagrammatic top view of a structured layer including a sacrificial layer and an ultrasound material layer in a stage of fabrication, according to aspects of the present disclosure.
Figure 6B:
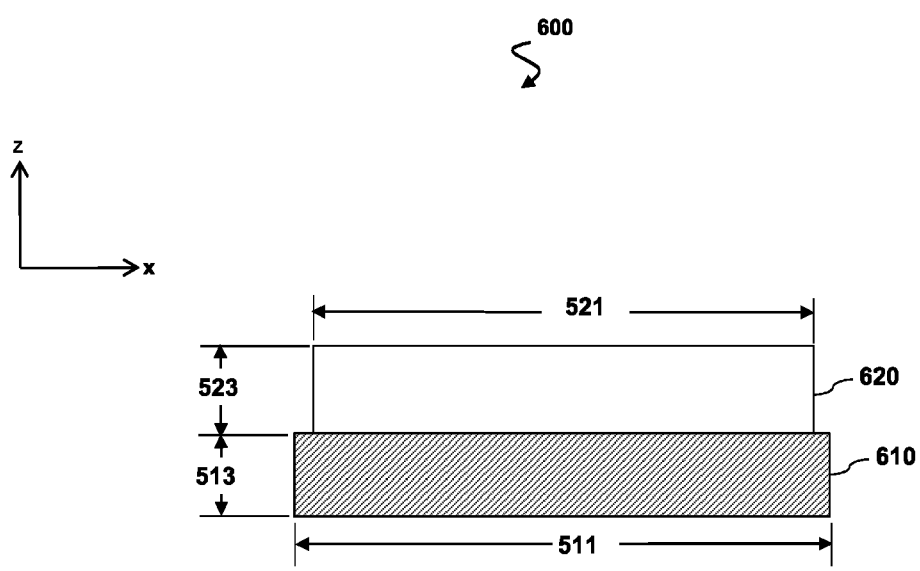
FIG. 6B is a diagrammatic cross-sectional view of a structured layer in a stage of fabrication, according to aspects of the present disclosure.
Figure 7:
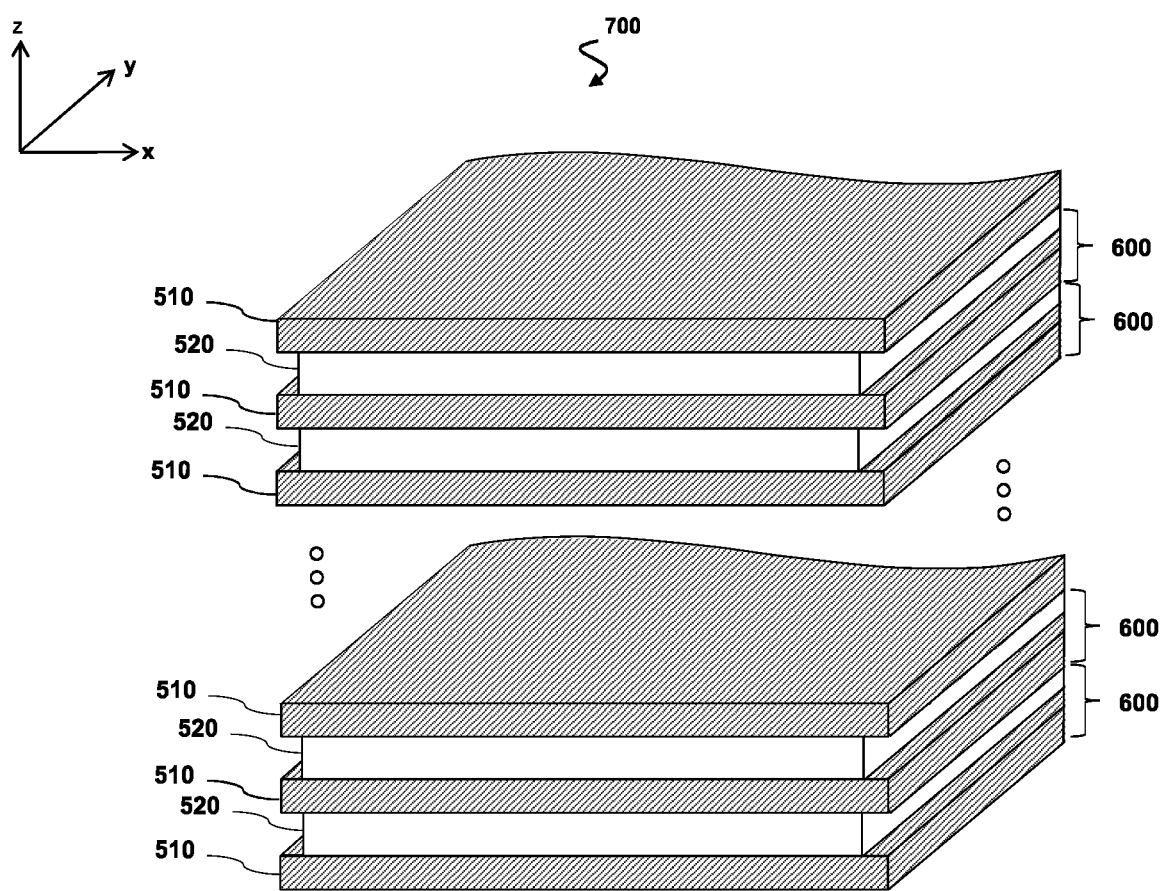
FIG. 7 is a diagrammatic perspective view of a stacked structure including a plurality of structured layers in a stage of fabrication, according to aspects of the present disclosure.
Figure 8:
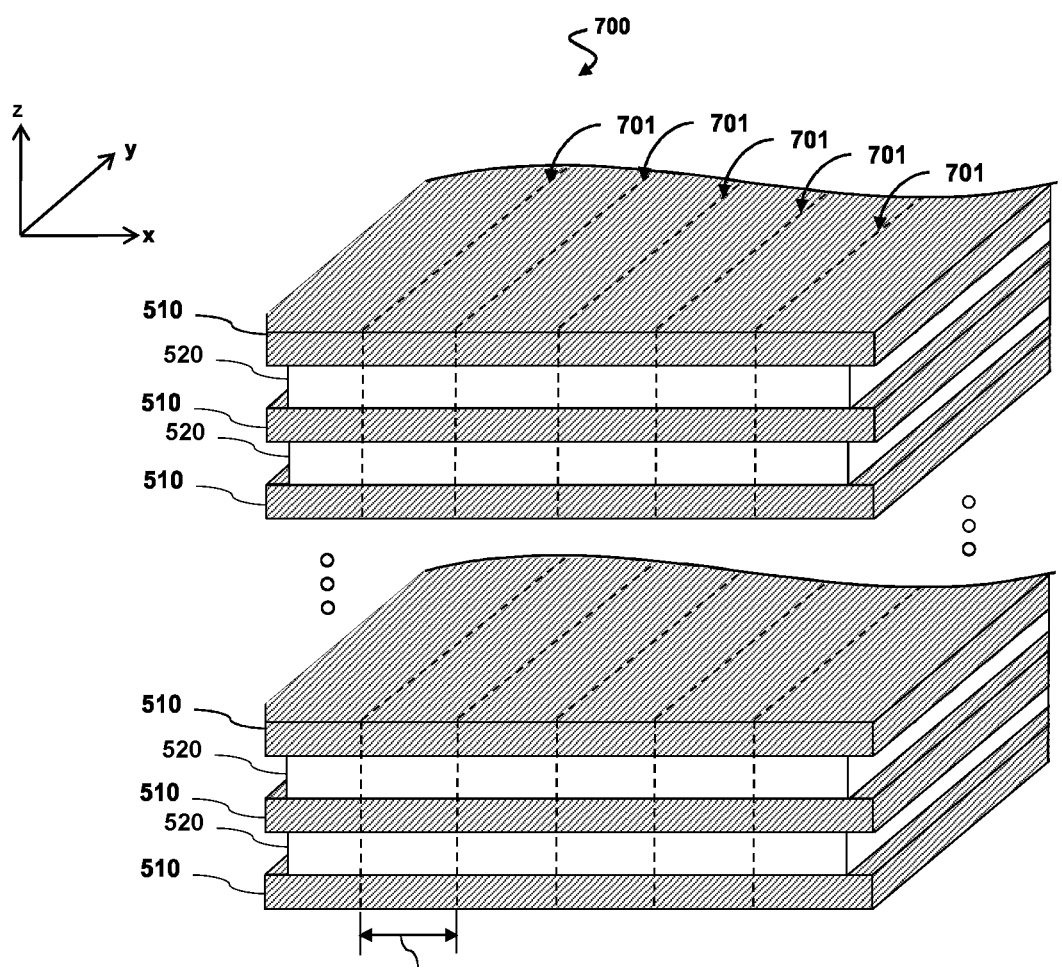
FIG. 8 is a diagrammatic perspective view of a stacked structure under first dicing in a stage of fabrication, according to aspects of the present disclosure.
Figure 9:
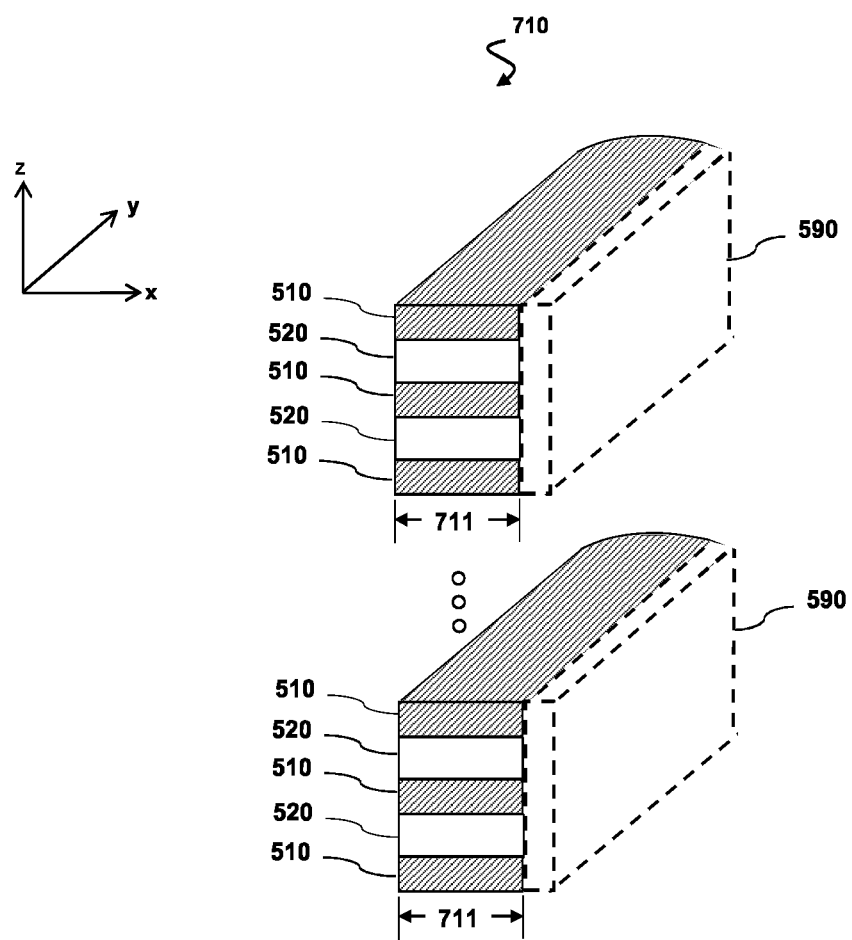
FIG. 9 is a diagrammatic perspective view of a diced structure in a stage of fabrication, according to aspects of the present disclosure.
Figure 10:
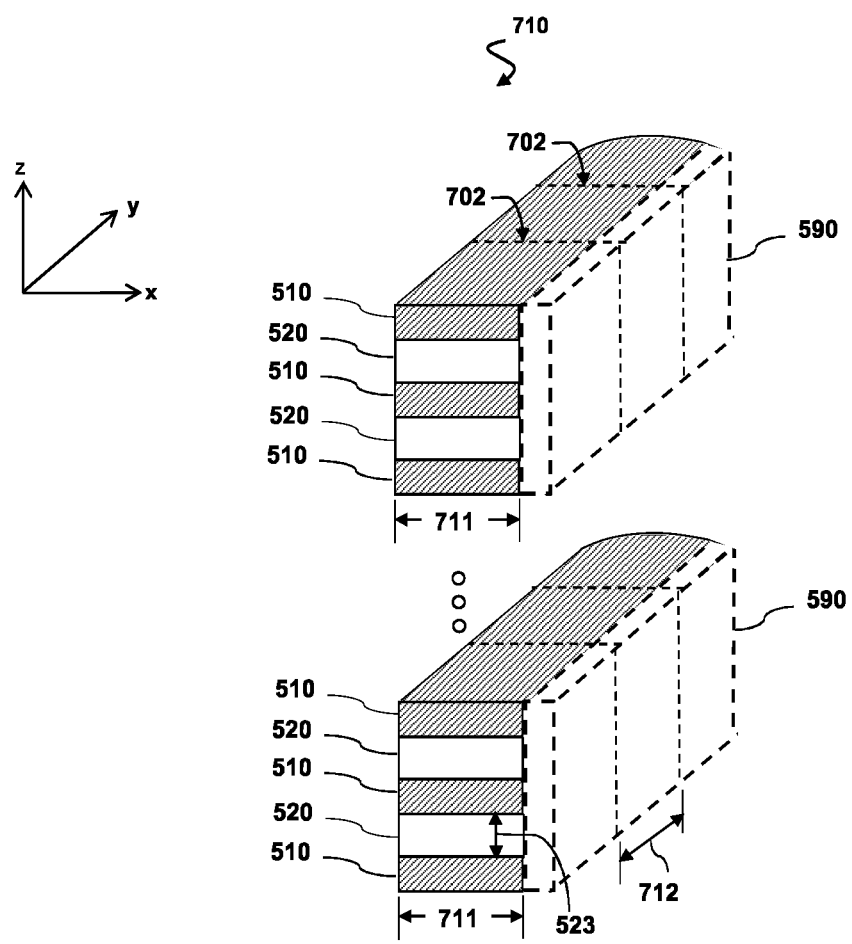
FIG. 10 is a diagrammatic perspective view of a diced structure under second dicing in a stage of fabrication, according to aspects of the present disclosure.
Figure 11:
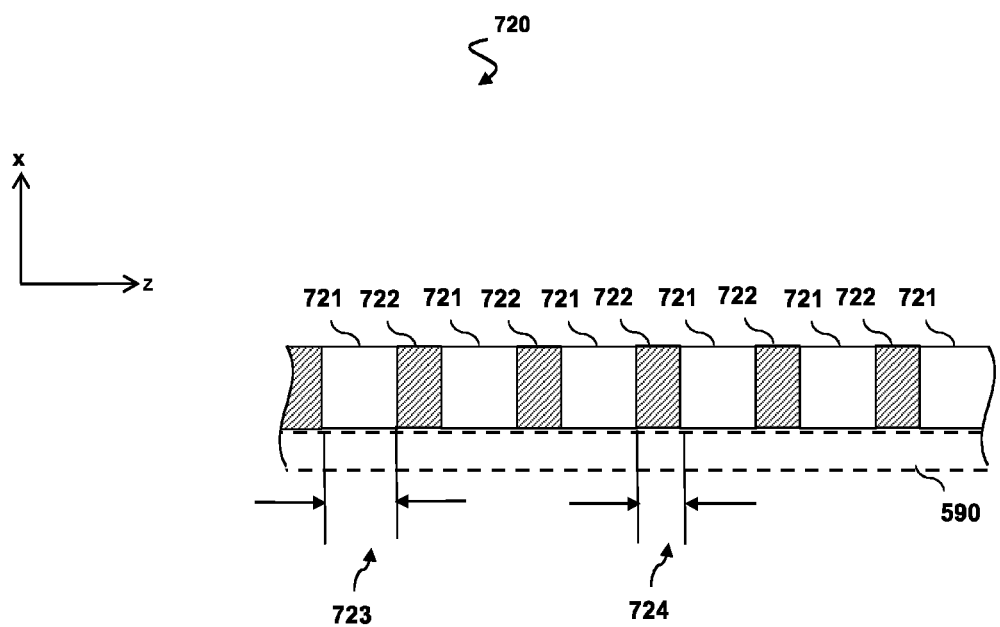
FIG. 11 is a diagrammatic top view of a portion of an elongated strip in a stage of fabrication, according to aspects of the present disclosure.
Figure 12:
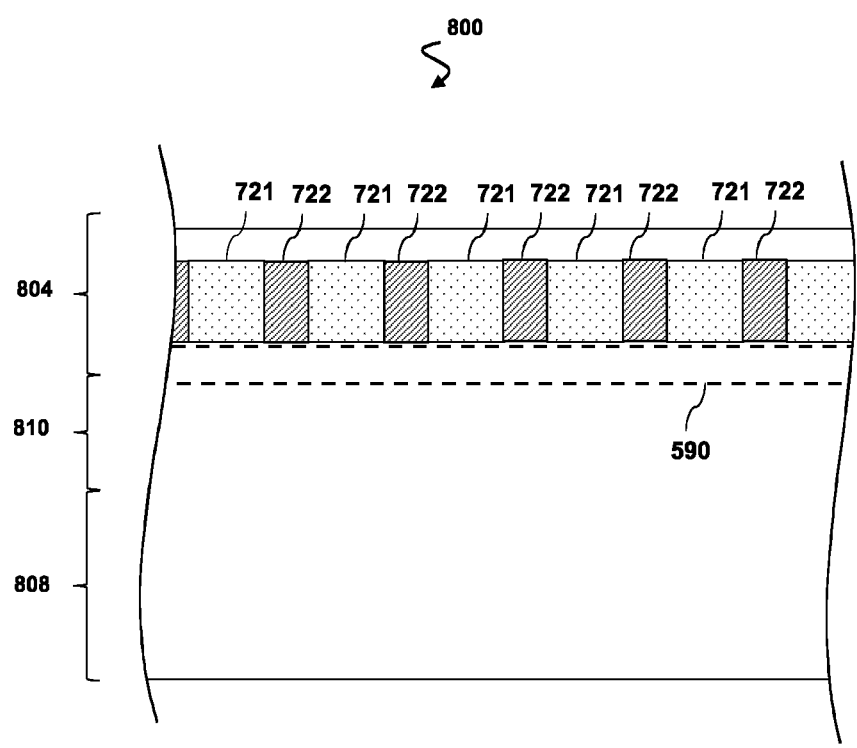
FIG. 12 is a diagrammatic top view of a portion of a flex circuit including an elongated strip in a stage of fabrication, according to aspects of the present disclosure.
Figure 13:
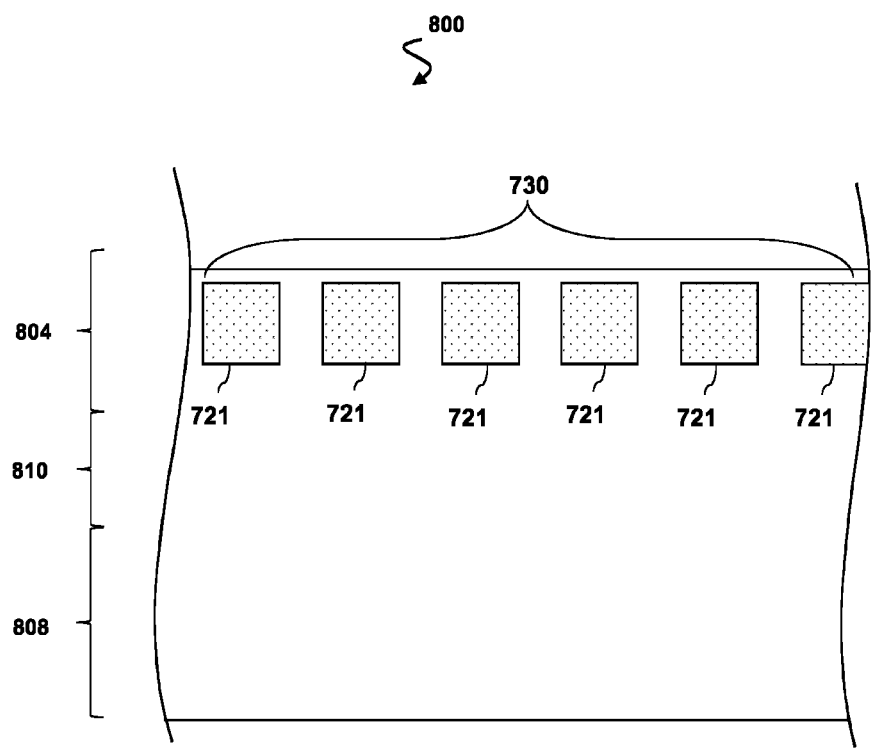
FIG. 13 is a diagrammatic top view of a portion a flex circuit including a transducer array formed from an elongated strip in a stage of fabrication, according to aspects of the present disclosure.

As described above, it is desirable to provide a phased array IVUS device capable of creating images high image resolution and/or quality while reducing or at least maintaining the size, usability, and stiff length of the device. A method 400 of manufacturing an intravascular imaging assembly substantially similar to the scanner assembly 110 is described with reference made to FIGS. 4-13. FIG. 4 is a flow diagram of a method 400 of fabricating an intravascular imaging assembly, leveraging semiconductor manufacturing techniques described herein, according to aspects of the disclosure. It is understood that additional steps can be provided before, during, and after the steps of method 400, and some of the steps described can be replaced or eliminated for other embodiments of the method. The steps of the method 400 can be carried out by a manufacturer of an IVUS device such as the IVUS device 102. FIG. 5A is a diagrammatic top view of a sacrificial material layer 510 in a stage of fabrication, according to aspects of the present disclosure. FIG. 5B is a diagrammatic cross-sectional view of the sacrificial material layer 510 taken along the line 501 of FIG. 5A in a stage of fabrication, according to aspects of the present disclosure. FIG. 6A is a diagrammatic top view of a structured layer 600 including the sacrificial layer 510 and an ultrasound material layer 520 in a stage of fabrication, according to aspects of the present disclosure. FIG. 6B is a diagrammatic cross-sectional view of the structured layer 600 taken along the line 601 of FIG. 6A in a stage of fabrication, according to aspects of the present disclosure. FIG. 7 is a diagrammatic perspective view of a stacked structure 700 including a plurality of the structured layers 600 in a stage of fabrication, according to aspects of the present disclosure. FIG. 8 is a diagrammatic perspective view of the stacked structure 700 under first dicing in a stage of fabrication, according to aspects of the present disclosure. FIG. 9 is a diagrammatic perspective view of a diced structure 710 in a stage of fabrication, according to aspects of the present disclosure. FIG. 10 is a diagrammatic perspective view of the diced structure 700 under second dicing in a stage of fabrication, according to aspects of the present disclosure. FIG. 11 is a diagrammatic top view of a portion of an elongated strip 720 in a stage of fabrication, according to aspects of the present disclosure. FIG. 12 is a diagrammatic top view of a portion of a flex circuit 800 including the elongated strip 720 in a stage of fabrication, according to aspects of the present disclosure. FIG. 13 is a diagrammatic top view of the portion the flex circuit 800 including a transducer array 730 formed from the elongated strip 720 in a stage of fabrication, according to aspects of the present disclosure.

Referring to the step 405 of the method 400 and FIGS. 5A and 5B, in an embodiment, a sacrificial material layer 510 is obtained. FIG. 5A is a diagrammatic top view of the sacrificial material layer 510. FIG. 5B is a diagrammatic cross-sectional view of the sacrificial material layer 510 taken along the line 501. For example, the top view is shown in an x-y plane and the cross-sectional view is shown in an x-z plane perpendicular to the x-y plane. The sacrificial material layer 510 can be composed from a group of sacrificial materials including silicon oxides and dioxides with various differing deposition and preparation techniques. Some examples may include low temperature chemical vapor deposition oxides, low pressure chemical vapor deposition oxides, or even sputtered oxides. Alternative options to silicon dioxide sacrificial layers may include aluminum, chromium, phosphosilicate glass, and borophosphosilicate glass. Dimensions of the sacrificial material layer 510 can vary in different embodiments. In some embodiments, the dimensions of the sacrificial material layer 510 may be dependent on capabilities of sacrificial layer deposition technologies. For example, the smallest deposition spot size may govern the minimum width and the minimum length of the sacrificial material layer 510. For example, the sacrificial material layer 510 can have a length 511 between about 5 micrometers (μm) and about 0.0127 meters (m), a width 512 between about 5 μm and about 0.0127 m, and a thickness 513 between about 0.01 μm and about 125 μm, where the upper limits of the length 511, the width 512, and the thickness 513 allows the sacrificial material layer 510 to produce transducer strips to cover circumference of a 12 Fr (French) catheter. The dimensions may also vary depending on dicing angles as described in greater detail below.

Referring to the step 410 of the method 400 and FIGS. 6A and 6B, in an embodiment, an ultrasound material layer 520 is disposed on top of the sacrificial material layer 510 to form a structured layer 600. FIG. 6A is a diagrammatic top view of the structured layer 600. FIG. 6B is a diagrammatic cross-sectional view of the structured layer 600 taken along the line 601. As shown, the ultrasound material layer 520 is disposed on top of the sacrificial material layer 510. The ultrasound material layer 520 can be composed from a group of ultrasound materials including PZT, polyvinylidene difluoride (PVDF), and their composites (e.g. PZT-PVDF, etc.). Dimensions of the ultrasound material layer 520 can vary in different embodiments. In some embodiments, the ultrasound material layer 520 can be thicker than the sacrificial material layer 510. For example, the ultrasound material layer 520 can have a length 521 between about 5 μm and about 0.0127 m, a width 522 between about 5 μm and about 0.0127 m, and a thickness 523 between about 5 μm and about 125 μm. As described in greater detail herein, the thickness 523 of the ultrasound material layer 520 defines the width of an individual ultrasound element in a transducer array such as the width 213 of an individual transducer 212 in the transducer array 124 and the thickness 513 of the sacrificial material layer 510 defines the pitch width in the transducer array such as the pitch width 211.

Referring to the step 415 of the method 400 and FIG. 7, in an embodiment, a plurality of the structured layers 600 is stacked to form a stacked structure 700. FIG. 7 is a diagrammatic perspective view of the stacked structure 700. As shown, the stacked structure 700 has a plurality of sacrificial material layers 510 disposed between a plurality of ultrasound material layers 520 in an alternating pattern. As described in greater detail herein, the number of structured layers 600 defines the number of transducers in a transducer array. For example, 32, 64, or 128 structured layers 600 can form transducer arrays with 32, 64, or 128 transducers, respectively. As such, the stacking can be repeated to form a stacked structure 700 with any suitable number of structured layers 600.

Referring to the step 420 of the method 400 and FIGS. 8 and 9, in an embodiment, first dicing is performed on the stacked structure 700 along a first plane to form a diced structure 710. FIG. 8 is a diagrammatic perspective view of the stacked structure 700 under the first dicing along the first plane as shown by the y-z plane. For example, the first dicing can include multiple first cuts 701 along the y-z plane separated by a distance 711. The first dicing can be performed using any suitable techniques. In some embodiments, the distance 711 can be between about 5 μm and about 2 millimeters (mm). As described in greater detail herein, the distance 711 defines the length of an individual ultrasound element. FIG. 9 is a diagrammatic perspective view of the diced structure 710. In some embodiments, after the first dicing, an additional sacrificial layer 590 may be formed adjacent to the diced structure 710 as shown by the dashed box. The additional sacrificial layer 590 can function as a spacer when forming a phased array with multiple rows of ultrasound elements as described in greater detail herein.

Referring to the step 425 of the method 400 and FIGS. 10 and 11, in an embodiment, second dicing is performed on the diced structure 710 along a second plane perpendicular to the first plane to form an elongated strip 720. FIG. 10 is a diagrammatic perspective view of the diced structure 700 under the second dicing along the second plane as shown by the x-z plane. For example, the second dicing can include multiple cuts 702 along the x-z plane separated by a distance 712. In some embodiments, the distance 712 can be between about 5 μm and about 2 mm. As described in greater detail herein, the distance 712 from the second dicing, the distance 711 from the first dicing, and the thickness 523 of the ultrasound material layers 520 define the height, the length, and the width of an individual ultrasound element. In some embodiments, the additional sacrificial layer 590 may be formed after the second dicing instead of after the first dicing. FIG. 11 is a diagrammatic top view of a portion of the elongated strip 720 in the x-z plane. The elongated strip 720 has an array of ultrasound elements 721 defined by portions of the sacrificial layers 510 separated by spacers 722 defined by portions of the ultrasound material layers 520. The width 723 of each ultrasound element 721 is defined by the thickness 523 of the ultrasound material layer 520. The ultrasound elements 721 are spaced apart by a pitch width 724 defined by the thickness 513 of the sacrificial material layer 510. In some embodiments, multiple elongated strips 720 may be stacked together to form a phased array with multiple rows, where the rows are separated by additional sacrificial layers 590. Thus, the sacrificial layers 510 and the additional sacrificial layers 590 control the horizontal spacing and vertical spacing, respectively, between the individual ultrasound elements.

Referring to the step 430 of the method 400 and FIG. 12, in an embodiment, the elongated strip 720 is coupled to a flex circuit 800 such as the flex circuit 214. FIG. 12 is a diagrammatic top view of a portion of the flex circuit 800 including the elongated strip 720. For example, the elongated strip 720 is directly disposed in a transducer region 804 of the flex circuit 800. The flex circuit 800 can include a transition region 810 interfacing the transducer region 804 to a controller region 808. The transducer region 804, the transition region 810, and the controller region 808 are substantially similar to the transducer region 204, the transition region 210, and the controller region 208, respectively.

Referring to the step 435 of the method 400 and FIG. 13, in an embodiment, the spacers 722 of the elongated strip 720 is removed from the flex circuit 800 to form a transducer array 730 on the flex circuit. FIG. 13 is a diagrammatic top view of the portion of the flex circuit 800 including the transducer array 730 formed from the ultrasound elements 721 of the elongated strip 720. As shown, the spacers 722 are removed from the flex circuit 800. The spacers 722 and the additional sacrificial layer 590 can be removed using any suitable semiconductor fabrication techniques such as etching. For example, photolithography can be used to define a pattern with openings matching the spacers 722, followed by various etching techniques including wet chemical etching using buffered oxide etch (e.g. Ammonium Fluoride+Hydrofluoric Acid), dry vapor etching (e.g. vapor HF, $H_2O$, HCl, HI, $Cl_2$, HI—HF, and etc.), reactive ion etching (if PZT structure and sacrificial layer combination has lower selectivity). The method 400 can include additional steps such as connecting the transducer array 730 to conductive traces such as the conductive traces 216 in the transition region 810 and controllers such as the controller chips 206 in the controller region 808.

In some instances, systems and methods of the invention may be applied to generate partial air kerfs between ultrasound elements, instead of complete spacing between elements. In such instances, the stacked structure is only partially diced (e.g. not completely through) at step 420. If partial kerfs are desired, the stacked structure (e.g., ultrasound material layers stacked and supported by sacrificial layers) is better able to disperse and absorb stress from mechanical dicing or enable better resolution of laser dicing by managing the heat distribution of the laser's spot size through the sacrificial material properties. A primary benefit is a potentially higher yield process than dicing through the more ultrasound material alone (often resulting in stress fractures for smaller dimensions), with a secondary benefit of possibly enabling a smaller kerf width design through laser.

Figure 14:
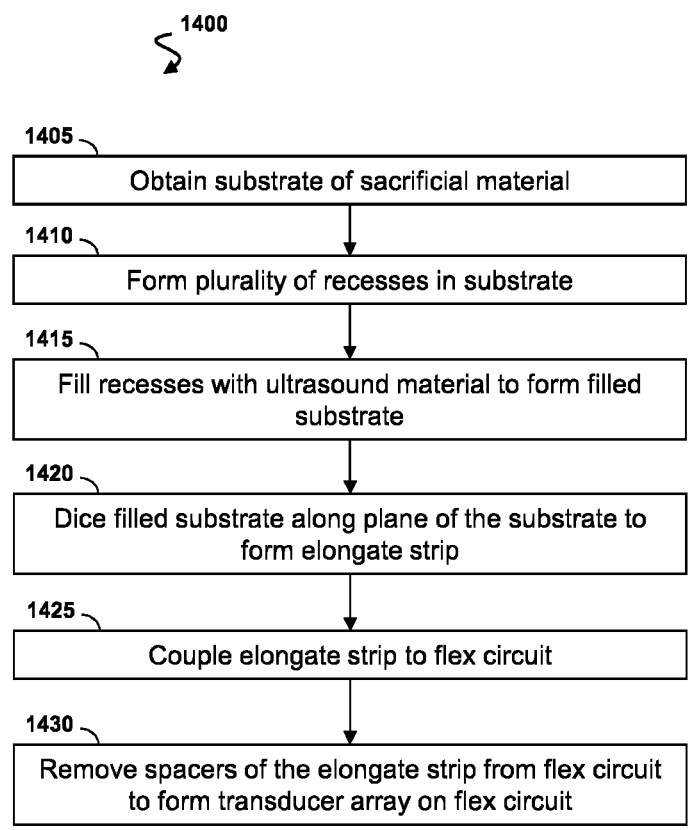
FIG. 14 is a flow diagram of a method of fabricating intravascular imaging assembly, leveraging semiconductor manufacturing techniques described herein, according to aspects of the disclosure.
Figure 15A:
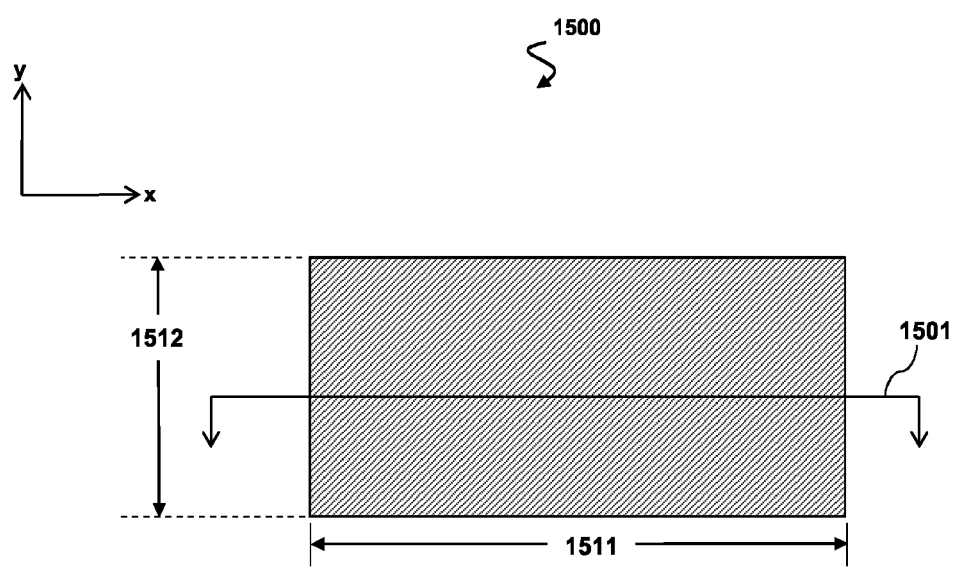
FIG. 15A is a diagrammatic top view of a substrate in a stage of fabrication, according to aspects of the present disclosure.
Figure 15B:
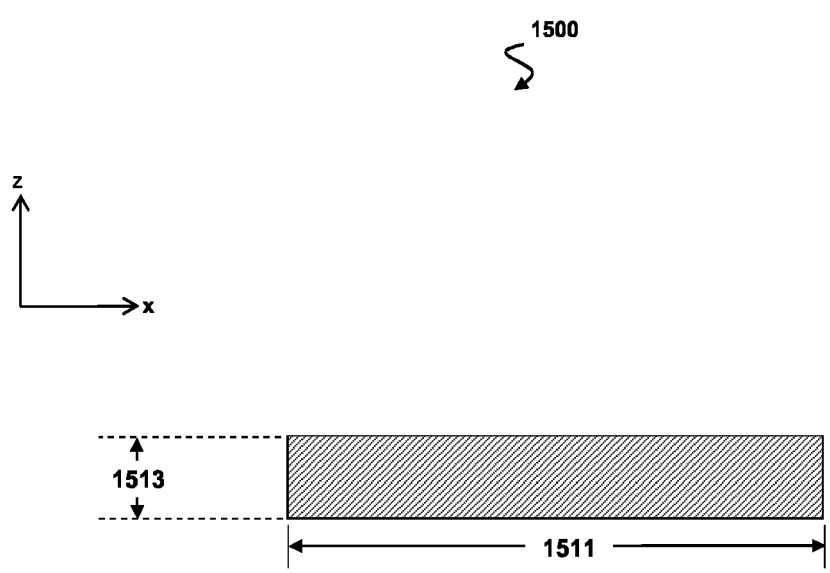
FIG. 15B is a diagrammatic cross-sectional view of a substrate in a stage of fabrication, according to aspects of the present disclosure.
Figure 16A:
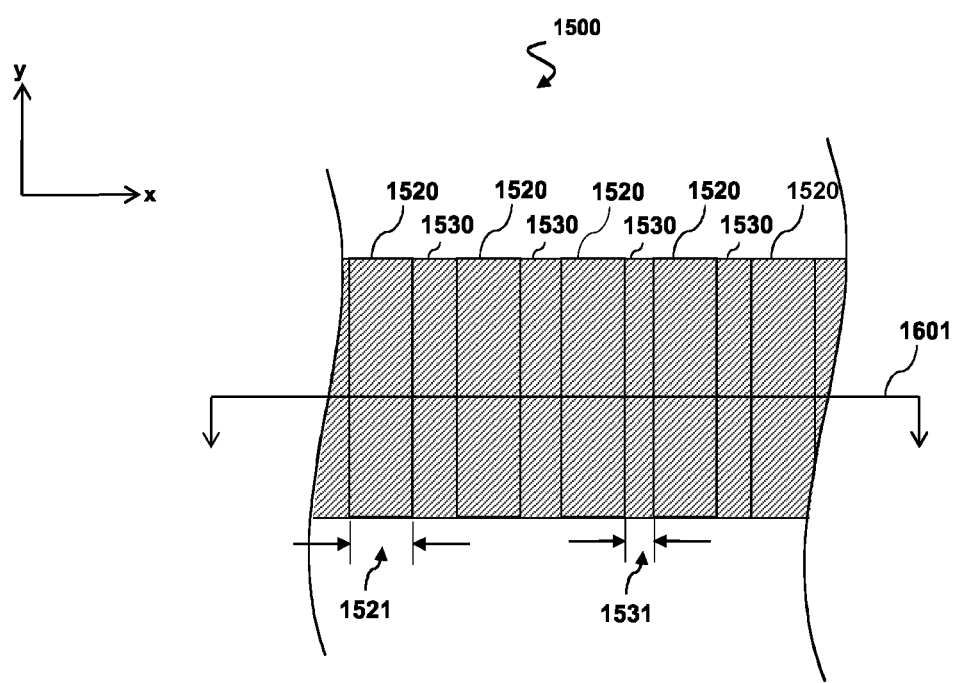
FIG. 16A is a diagrammatic top view of a portion of a substrate having patterned recesses in a stage of fabrication, according to aspects of the present disclosure.
Figure 16B:
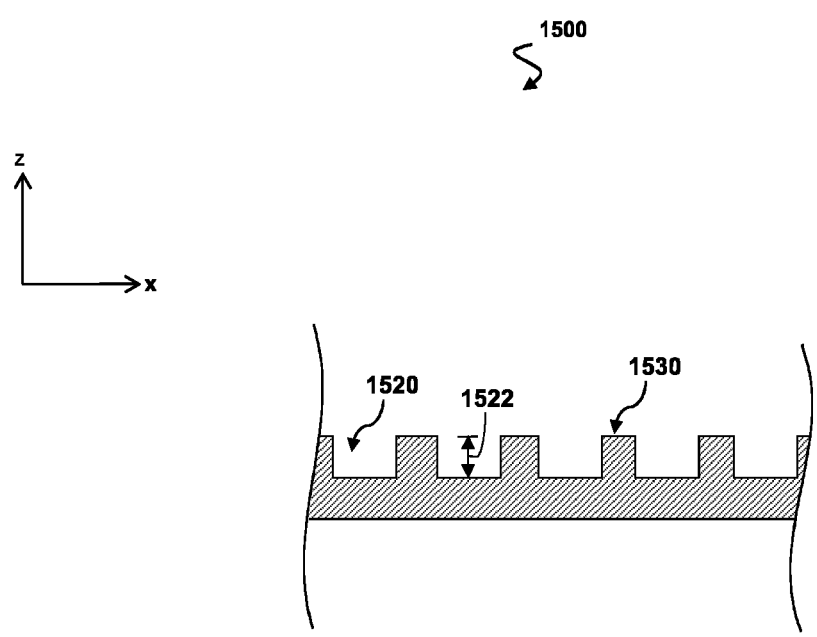
FIG. 16B is a diagrammatic cross-sectional view of a portion of a substrate having patterned recesses in a stage of fabrication, according to aspects of the present disclosure.
Figure 17:
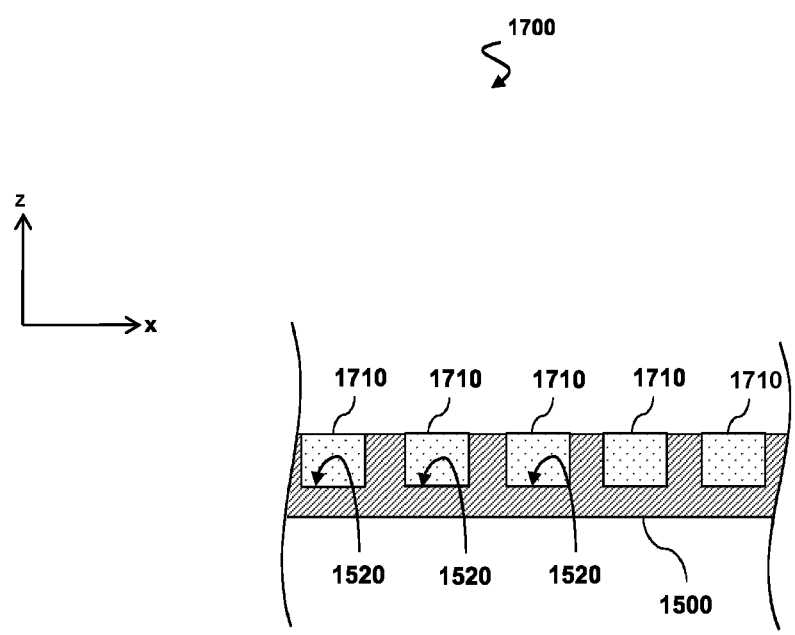
FIG. 17 is a diagrammatic cross-sectional view of a portion of a filled substrate in a stage of fabrication, according to aspects of the present disclosure.
Figure 18:
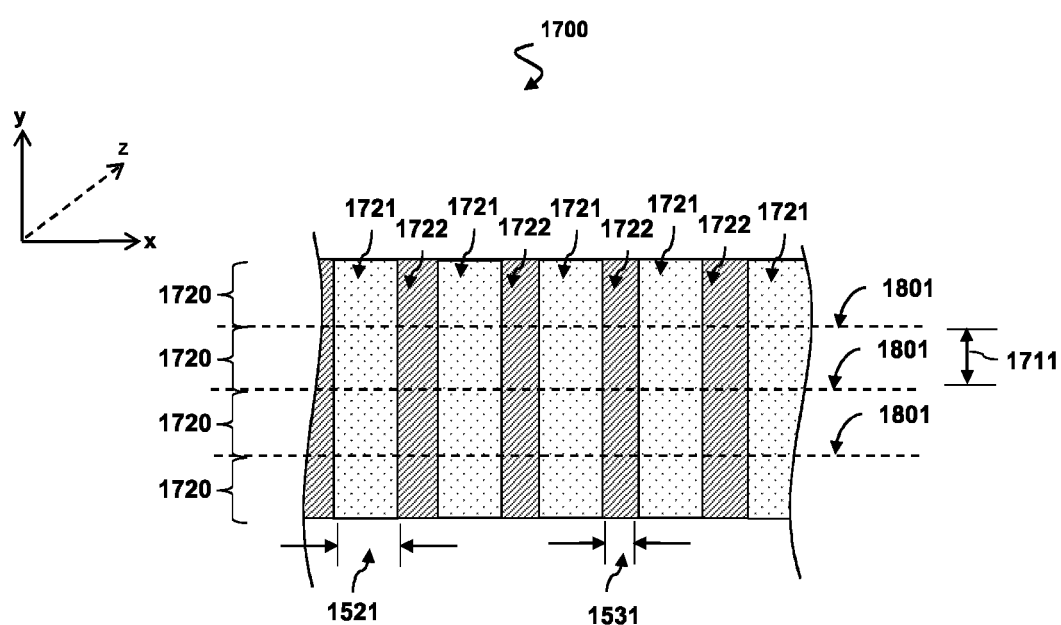
FIG. 18 is a diagrammatic cross-sectional view of a portion of a filled substrate under dicing in a stage of fabrication, according to aspects of the present disclosure.

A method 1400 of manufacturing an intravascular imaging assembly substantially similar to the scanner assembly 110 is described with reference made to FIGS. 14-18. FIG. 14 is a flow diagram of a method 1400 of fabricating an intravascular imaging assembly, leveraging semiconductor manufacturing techniques described herein, according to aspects of the disclosure. It is understood that additional steps can be provided before, during, and after the steps of method 1400, and some of the steps described can be replaced or eliminated for other embodiments of the method. The steps of the method 1400 can be carried out by a manufacturer of an IVUS device such as the IVUS device 102. FIG. 15A is a diagrammatic top view of a substrate 1500 in a stage of fabrication, according to aspects of the present disclosure. FIG. 15B is a diagrammatic cross-sectional view of the substrate 1500 taken along the line 1501 of FIG. 15A in a stage of fabrication, according to aspects of the present disclosure. FIG. 16A is a diagrammatic top view of a portion of the substrate 1500 having patterned recesses 1520 in a stage of fabrication, according to aspects of the present disclosure. FIG. 16B is a diagrammatic cross-sectional view of a portion of the substrate 1500 having the patterned recesses 1520 taken along the line 1601 of FIG. 16A in a stage of fabrication, according to aspects of the present disclosure. FIG. 17 is a diagrammatic cross-sectional view of a portion of a filled substrate 1700 taken along the line 1601 of FIG. 16A in a stage of fabrication, according to aspects of the present disclosure. FIG. 18 is a diagrammatic cross-sectional view of a portion of the filled substrate 1700 under dicing in a stage of fabrication, according to aspects of the present disclosure.

Referring to the step 1405 of the method 1400 and FIGS. 15A and 15B, in an embodiment, a substrate 1500 of a sacrificial material is obtained. FIG. 15A is a diagrammatic top view of the substrate 1500. FIG. 15B is a diagrammatic cross-sectional view of the substrate 1500 taken along the line 1501. For example, the top view is shown in an x-y plane and the cross-sectional view is shown in an x-z plane perpendicular to the x-y plane. The sacrificial material of the substrate 1500 can be substantially similar to the material of the sacrificial material layer 510. Dimensions of the substrate 1500 can vary in different embodiments. For example, the substrate 1500 can have a length 1511 between about 10 μm and about 2 centimeters (cm), a width 1512 between about 10 μm and about 2 cm, and a thickness 1513 between about 5 μm and about 50 μm. The length 511 may be selected to be about twice the smallest dice width. The thickness 1513 may be selected to accommodate recesses 1520, which may be sized and shaped according to pre-determined transducer dimensions, as described in greater detail herein. For example, the thickness 1513 can be about the same as the sum of the thickness 513 of the sacrificial material layer 510 and the thickness 523 of the ultrasound material layer 520.

Referring to the step 1410 of the method 1400 and FIGS. 16A and 16B, in an embodiment, a plurality of recesses 1520 is formed in the substrate 1500. The forming or patterning of the recesses 1520 in the substrate 1500 can use any suitable semiconductor fabrication techniques. For example, the forming or patterning can include transferring a photo pattern with openings that define the recesses 1520 onto the substrate 1500 via photolithography and removing sacrificial material from the substrate 1500 according to the openings via etching. An example of a suitable etching process may be deep reactive-ion etching (DRIE).

FIG. 16A is a diagrammatic top view of a portion of the substrate 1500 having the patterned recesses 1520. As shown, the recesses 1520 are separated by ribs 1530. For example, the recesses 1520 and the ribs 1530 extend along a y-axis of the substrate 1500. FIG. 16B is a diagrammatic cross-sectional view of a portion of the substrate 1500 having the patterned recesses 1520 taken along the line 1601. For example, the cross-sectional view is shown in an x-z plane perpendicular to the x-y plane. Dimensions of the recesses 1520 and the ribs 1530 can vary in different embodiments. For example, the ribs 1530 can have a width 1531 between about 5 μm and about 2 mm and the recesses 1520 can have a width 1521 between about 5 μm and about 125 μm and a depth or height 1522 between about 5 μm and about 125 μm. As described in greater detail herein, the width 1521 and the height 1522 of the recesses 1520 can define dimensions of an individual ultrasound element in a transducer array and the width 1531 can define a pitch width between the ultrasound elements in the transducer array.

Referring to the step 1415 of the method 1400 and FIG. 17, in an embodiment, the plurality of recesses 1520 is filled with an ultrasound material 1710 to form a filled substrate 1700. FIG. 17 is a diagrammatic cross-sectional view of a portion of the filled substrate 1700 taken along the line 1601, where the recesses 1520 are filled with the ultrasound material 1710. The ultrasound material 1710 can be substantially similar to the material of the ultrasound material layer 520.

Referring to the step 1420 of the method 1400 and FIG. 18, in an embodiment, the filled substrate 1700 is diced along a plane of the filled substrate 1700 to form elongated strips 1720 similar to the elongated strip 720. FIG. 18 is a diagrammatic top view of a portion of the filled substrate 1700 under the dicing along the plane as shown by the x-z plane. For example, the dicing can include multiple cuts 1801 along the x-z plane separated by a distance 1711. Each elongated strip 1720 has an array of ultrasound elements 1721 similar to the ultrasound elements 721 defined by the ultrasound material 1710 and spacers 1722 similar to the spacers 722 defined by the sacrificial material of the substrate 1500. The distance 1711 and the width 1521 of the recesses 1520 define the length and the width, respectively, of the ultrasound elements 1721. The width 1531 of the ribs 1530 defines the pitch width between the ultrasound elements 1721.

Referring to the step 1425, in an embodiment, the elongated strip 1720 is coupled to a flex circuit similar to the flex circuits 214 and 800. For example, the coupling can be similar to the step 430 of the method 400 and as shown in FIG. 12.

Referring to the step 1430, in an embodiment, the spacers 1722 of the elongated strip 1720 are removed from the flex circuit. For example, the removing can be similar to the step 435 of the method 400 and as shown in FIG. 13.

In some embodiments, the method 1400 can be combined with the stacking mechanisms described in the method 400. For example, the method 1400 can additionally include stacking a plurality of the filled substrate 1700 to form a stacked structure and dicing the stacked structure along a first plane followed by a second plane perpendicular to the first plane.

The forming of the recesses 1520 at the step 1410 can be performed to create transducer arrays with transducers of any size and arranged in any configuration. For example, each individual recess can be sized and shaped according to pre-determined transducer dimensions and the recesses can be arranged to facilitate creation of images at a pre-determined resolution and/or vasculature view.

Figure 19A:
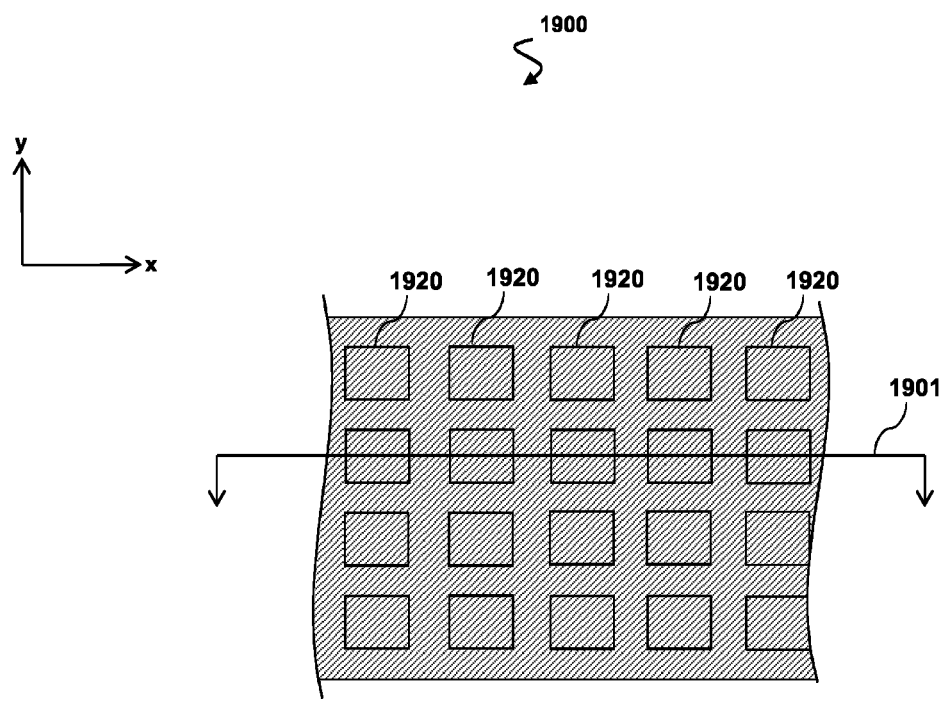
FIG. 19A is a diagrammatic top view of a portion of a substrate including aligned recesses, according to aspects of the present disclosure.
Figure 19B:
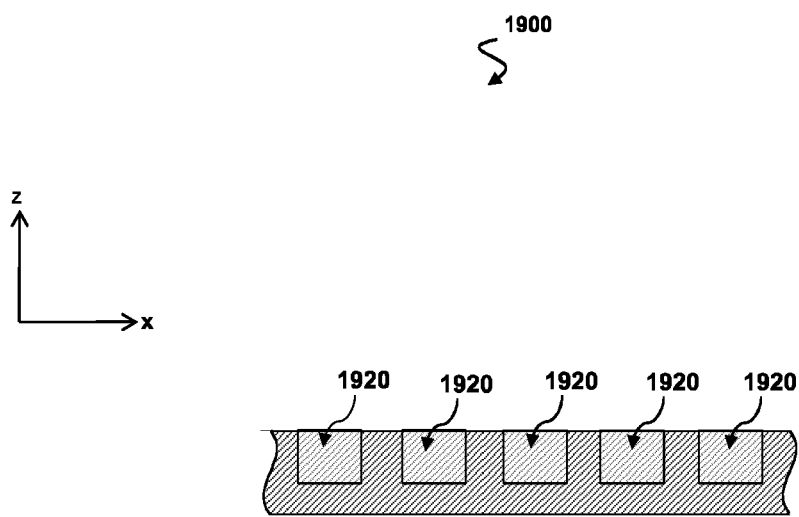
FIG. 19B is a diagrammatic cross-sectional view of a portion of a substrate including the aligned recesses, according to aspects of the present disclosure.
Figure 20A:
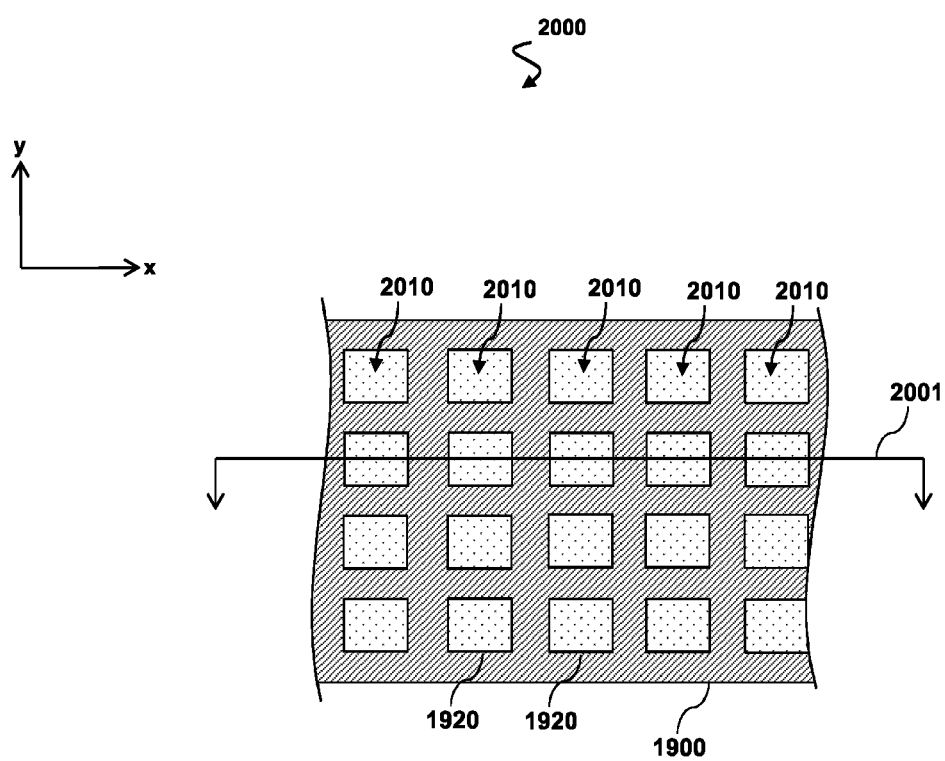
FIG. 20A is a diagrammatic top view of a portion of a filled substrate, according to aspects of the present disclosure.
Figure 20B:
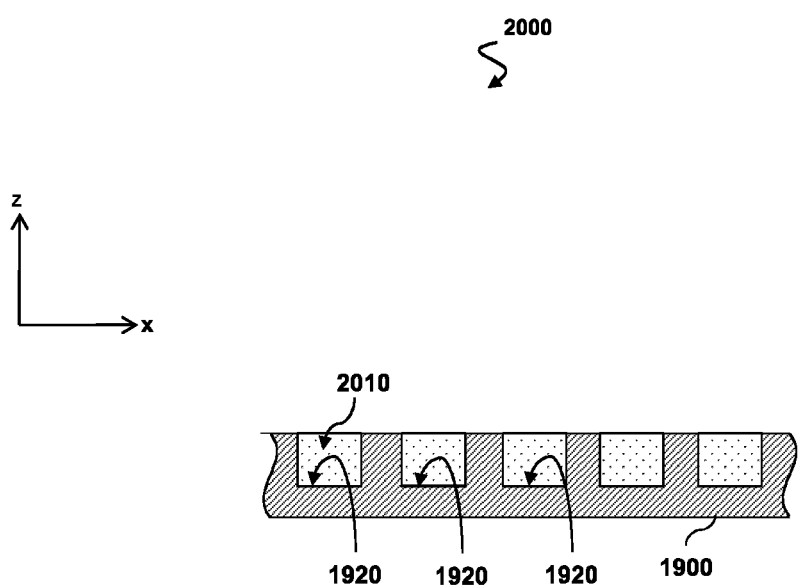
FIG. 20B is a diagrammatic cross-sectional view of a portion of a filled substrate, according to aspects of the present disclosure.
Figure 21:
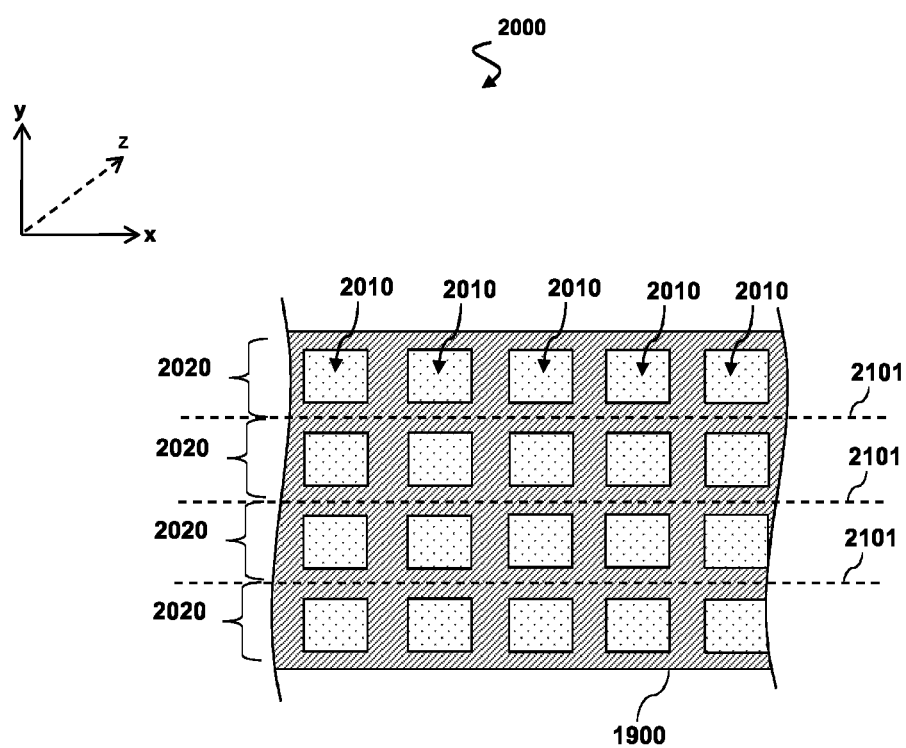
FIG. 21 is a diagrammatic top view of a portion of a filled substrate under dicing, according to aspects of the present disclosure.
Figure 22A:
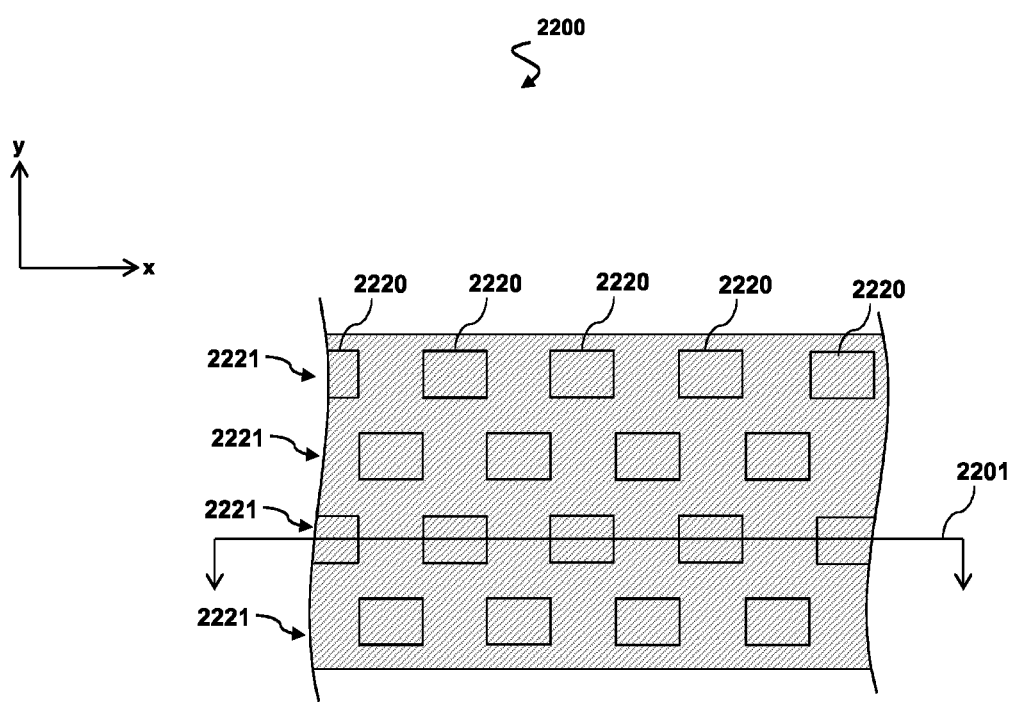
FIG. 22A is a diagrammatic top view of a portion of a substrate including offset recesses, according to aspects of the present disclosure.
Figure 22B:
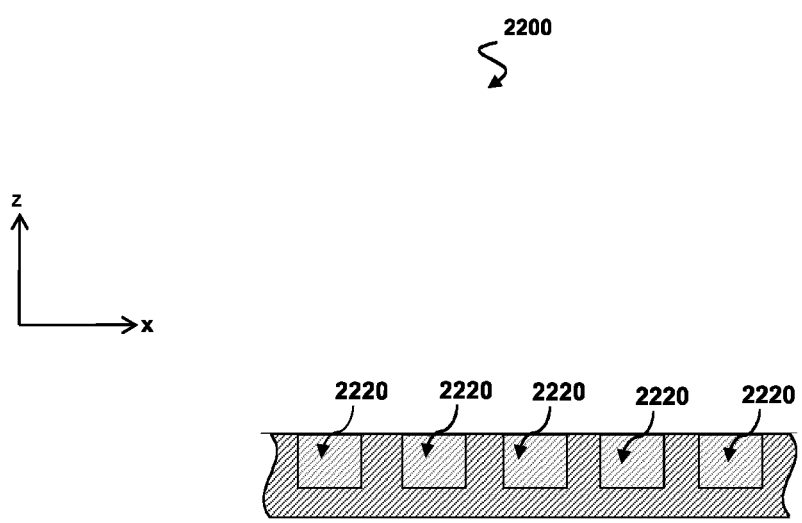
FIG. 22B is a diagrammatic cross-sectional view of a portion of a substrate with offset recesses, according to aspects of the present disclosure.

FIGS. 19-21 collectively illustrate an embodiment of forming recesses in an aligned configuration. FIG. 19A is a diagrammatic top view of a portion of a substrate 1900 including aligned recesses 1920, according to aspects of the present disclosure. The substrate 1900 is composed of similar sacrificial material as the sacrificial material layer 500 and the substrate 1500. The recesses 1920 are formed on the substrate 1900 using similar mechanisms as the forming of the recesses 1520. The recesses 1920 are uniform in size and shape. The recesses 1920 are arranged in a plurality of rows and are aligned across rows separated by sacrificial material of the substrate 1900. Each recess 1920 defines a transducer. Dimensions of the recesses 1920 can vary in different embodiments. In some embodiments, to create a transducer array with 64 transducers for a 3.0 Fr IVUS device 102, each recess 1920 can include a length between about 0.5 mm and about 1.5 mm, a width between about 15 μm and about 30 μm, and a height between 50 μm and about 80 μm, and adjacent recesses 1920 can be separated by a distance between about 15 μm and about 30 μm. FIG. 19B is a diagrammatic cross-sectional view of a portion of the substrate 1900 including the aligned recesses 1920 taken along the line 1901 of FIG. 19A, according to aspects of the present disclosure. For example, the top view is shown in an x-y plane and the cross-sectional view is shown in an x-z plane perpendicular to the x-y plane.

FIG. 20A is a diagrammatic top view of a portion of a filled substrate 2000, according to aspects of the present disclosure. The filled substrate 2000 is formed by filling the recesses 1920 of the substrate 1900 with an ultrasound material 2010 similar to the ultrasound material 1710. FIG. 20B is a diagrammatic cross-sectional view of a portion of the filled substrate 2000 taken along the line 2001 of FIG. 20A, according to aspects of the present disclosure.

FIG. 21 is a diagrammatic top view of a portion of the filled substrate 2000 under dicing, according to aspects of the present disclosure. The dicing can include multiple cuts 2101 along an x-z plane perpendicular to the x-y plane. The dicing forms elongated strips 2020 similar to the elongated strips 720 and 1720. The encasing or surrounding of the ultrasound material 2010 by the sacrificial material of the substrate 1900 can reduce the mechanical stress of dicing. In some embodiments, laser cut can be used to further reduce the risk of fracturing or damaging the ultrasound material 2010. After the dicing, similar to the methods 400 and 1400, an elongated strip 2020 can be coupled to a flex circuit such as the flex circuits 214 and 800 and the sacrificial material of the elongated strips 2020 can be removed to form a transducer array on the flex circuit.

FIGS. 22-27 collectively illustrate an embodiment of forming recesses in an offset configuration. FIG. 22A is a diagrammatic top view of a portion of a substrate 2200 including offset recesses 2220, according to aspects of the present disclosure. The substrate 2200 is similar to the substrates 1500 and 1900. The recesses 2220 are formed on the substrate 2200 using similar mechanisms as the forming of the recesses 1520 and 1920. As shown, the recesses 2220 are arranged in an offset pattern, where placements of the recesses 2220 in adjacent series or rows 2221 are offset from each other. The offset pattern or configuration allows for concurrent capture of images of different longitudinal portions of the vessel 120. FIG. 22B is a diagrammatic cross-sectional view of a portion of the substrate 2200 with the offset recesses 2220 taken along the line 2201 of FIG. 22A, according to aspects of the present disclosure.

Figure 23A:
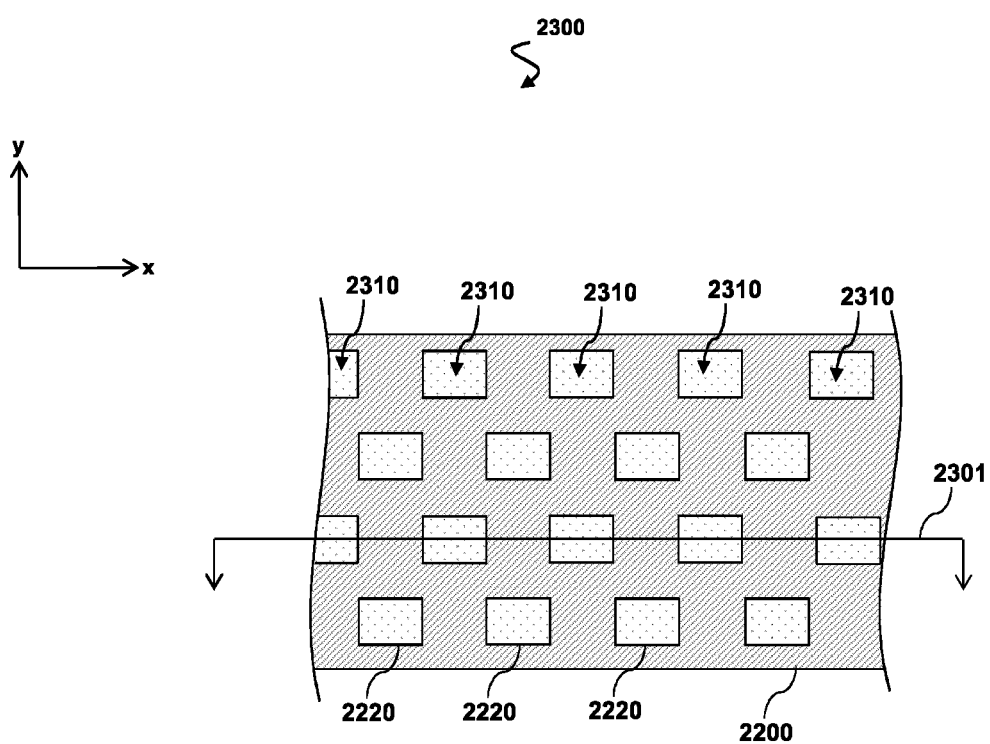
FIG. 23A is a diagrammatic top view of a portion of a filled substrate, according to aspects of the present disclosure.
Figure 23B:
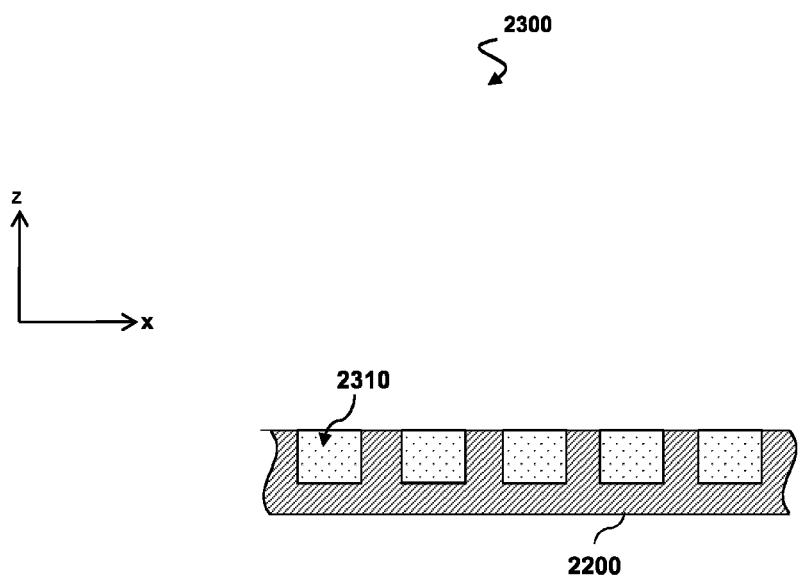
FIG. 23B is a diagrammatic cross-sectional view of a portion of a filled substrate, according to aspects of the present disclosure.

FIG. 23A is a diagrammatic top view of a portion of a filled substrate 2300, according to aspects of the present disclosure. The filled substrate 2300 is formed by filling the recesses 2220 of the substrate 2200 with an ultrasound material 2310 similar to the ultrasound material 1710 and 2010. FIG. 23B is a diagrammatic cross-sectional view of a portion of the filled substrate 2300 taken along the line 2301 of FIG. 23A, according to aspects of the present disclosure.

Figure 24:
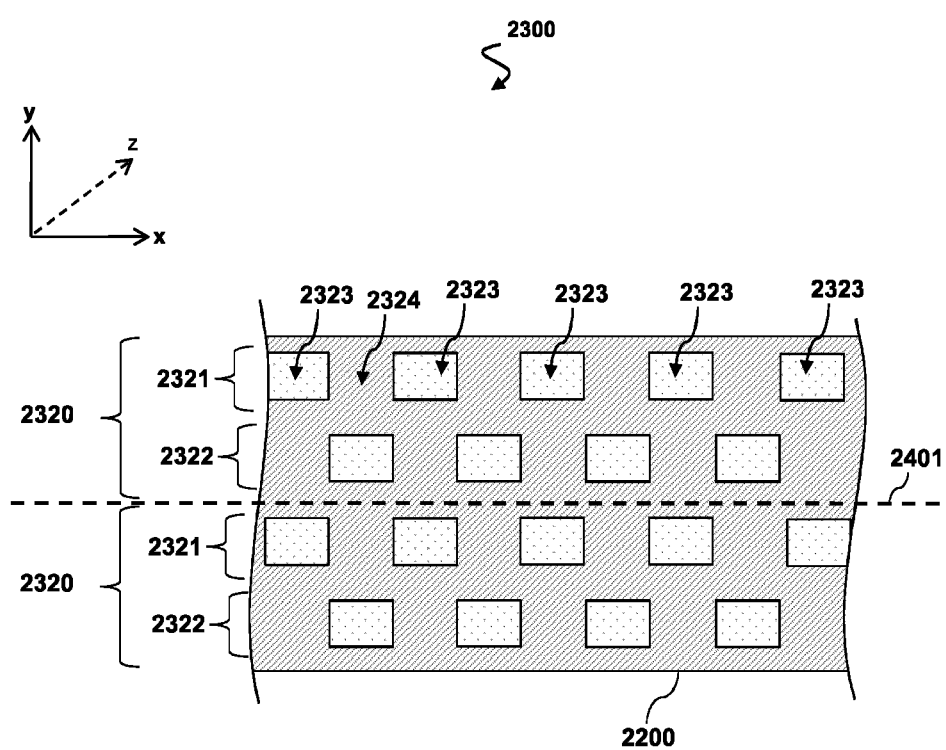
FIG. 24 is a diagrammatic top view of a portion of a filled substrate under dicing, according to aspects of the present disclosure.
Figure 25:
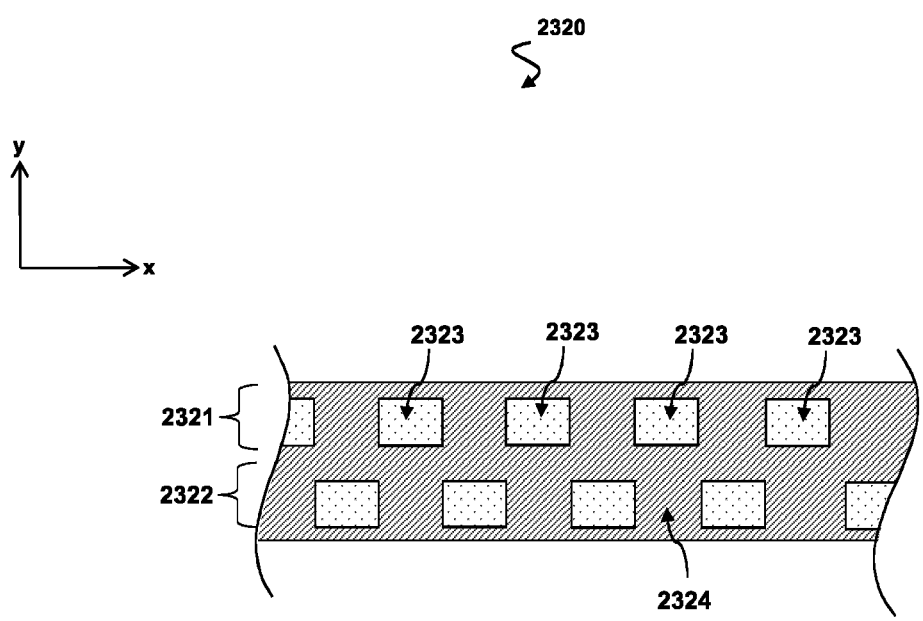
FIG. 25 is a diagrammatic top view of a portion of an elongated strip, according to aspects of the present disclosure.

FIG. 24 is a diagrammatic top view of a portion of the filled substrate 2300 under dicing, according to aspects of the present disclosure. The dicing can include one or more cuts 2401 along an x-z plane perpendicular to the x-y plane. The dicing forms elongated strips 2320 including two series 2321 and 2322 of ultrasound elements 2323 defined by the ultrasound material 2310 and spacers 2324 defined by material of the substrate 2200. The positions of the ultrasound elements 2323 of the two series 2321 and 2322 are offset from each other. FIG. 25 is a diagrammatic top view of a portion of the elongated strip 2320, according to aspects of the present disclosure.

Figure 26:
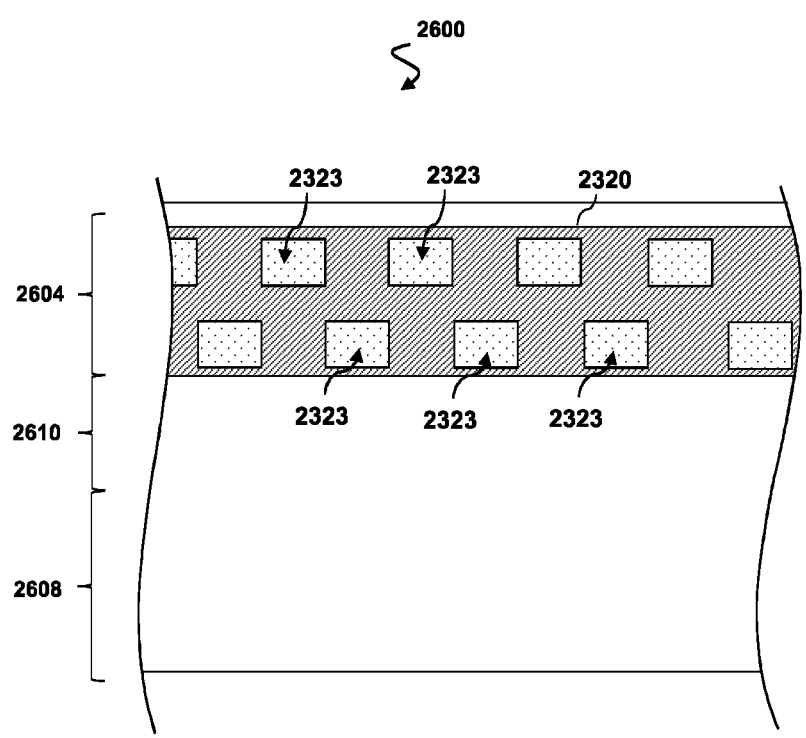
FIG. 26 is a diagrammatic top view of a portion of a flex circuit including an elongated strip, according to aspects of the present disclosure.

FIG. 26 is a diagrammatic top view of a portion a flex circuit 2600 similar to the flex circuits 214 and 800 including the elongated strip 2320, according to aspects of the present disclosure. The flex circuit 2600 includes a transition region 2610 positioned between a transducer region 2604 and a controller region 2608. The elongated strip 2320 can be coupled to the flex circuit 2600 using similar mechanisms as in the step 1425. For example, the elongated strip 2320 is directly disposed on the transducer region 2604 of the flex circuit 2600.

Figure 27:
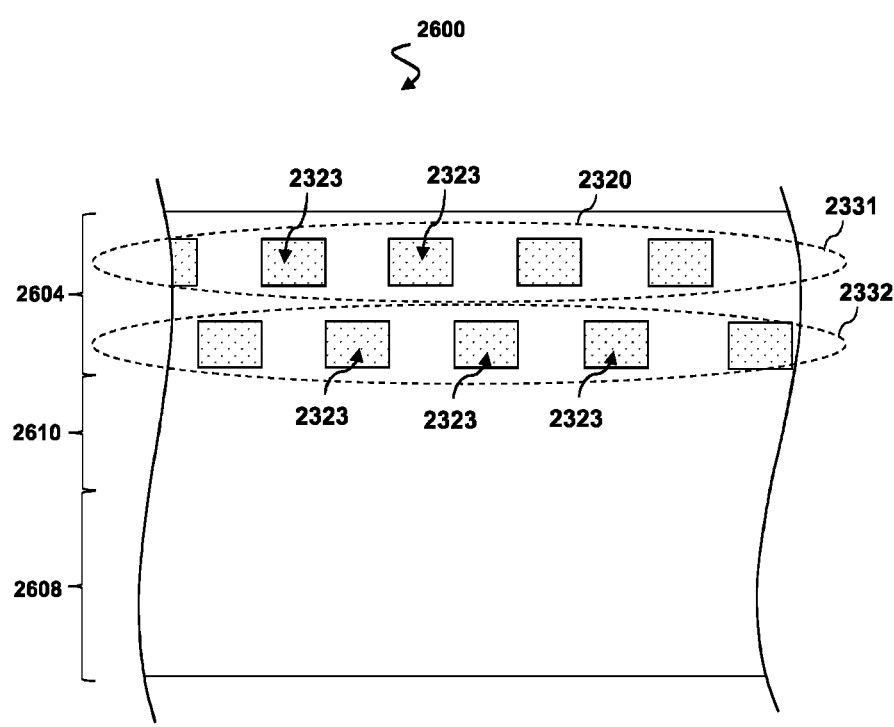
FIG. 27 is a diagrammatic top view of a portion of a flex circuit including transducer arrays formed from an elongated strip, according to aspects of the present disclosure.

FIG. 27 is a diagrammatic top view of the portion of the flex circuit 2600 including transducer arrays 2331 and 2332 formed from the elongated strip 2320, according to aspects of the present disclosure. For example, after the elongated strip 2320 is coupled to the flex circuit 2600, the spacers 2324 are removed from the flex circuit 2600 using similar mechanisms as in the step 1430. The flex circuit 2600 can be wrapped around the support member 230 such that the ultrasound elements 2323 are positioned at circumferences of the support member 230. For example, the transducer array 2331 is positioned around one circumference and the transducer array 2332 is positioned around another circumference spaced from the transducer array 2332 along a longitudinal axis of the support member 230. By shifting the positions of the recesses 2220 to create shifted ultrasound elements 2323 in the transducer arrays 2331 and 2332 and/or including more transducer arrays on the flex circuit 2600, various methods of beamforming such as dynamic focusing and expanding aperture can be performed to improve image quality.

Figure 28:
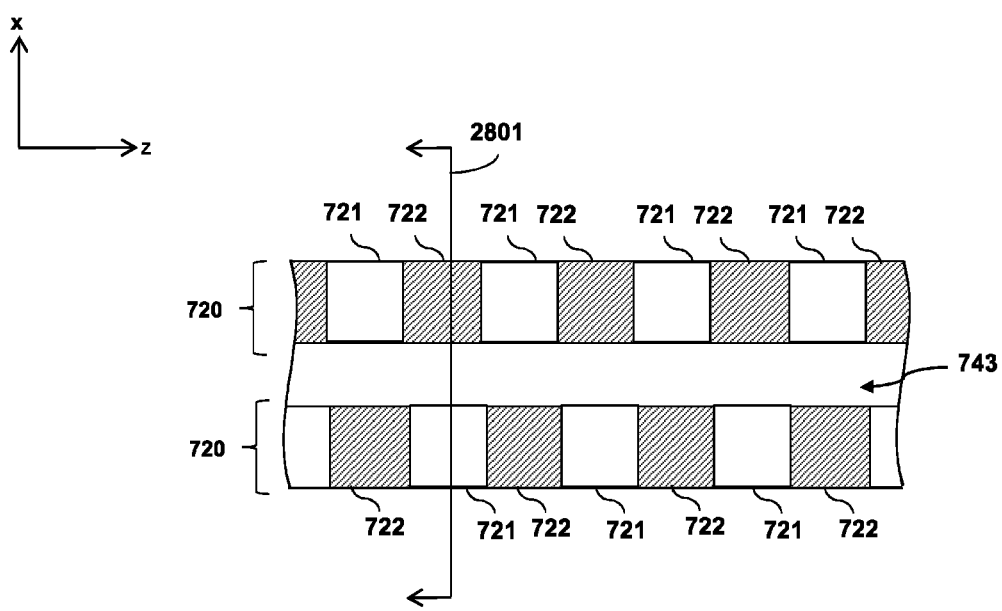
FIG. 28 is a diagrammatic top view of a portion of a combined strip including two elongated strips arranged in an offset configuration in a stage of fabrication, according to aspects of the present disclosure.

In an embodiment, the method 400 may be employed to form a multi-transducer array having multiple transducer arrays similar to the transducer arrays 730, 2331 and 2332. FIGS. 28-31 collectively illustrate an embodiment of forming a multi-transducer array. FIG. 28 is a diagrammatic top view of a portion of two elongated strips 720 arranged in an offset configuration in a stage of fabrication, according to aspects of the present disclosure. As described above, the first dicing and the second dicing of the stacked structure 700 can form a plurality of elongated strips 720. The two elongate strips 720 can be positioned such that the two elongated strips 720 are about parallel and separated by a gap 743 and the ultrasound elements 721 of one elongated strip 720 are offset from the ultrasound elements 721 of the other elongated strip 720.

Figure 29:
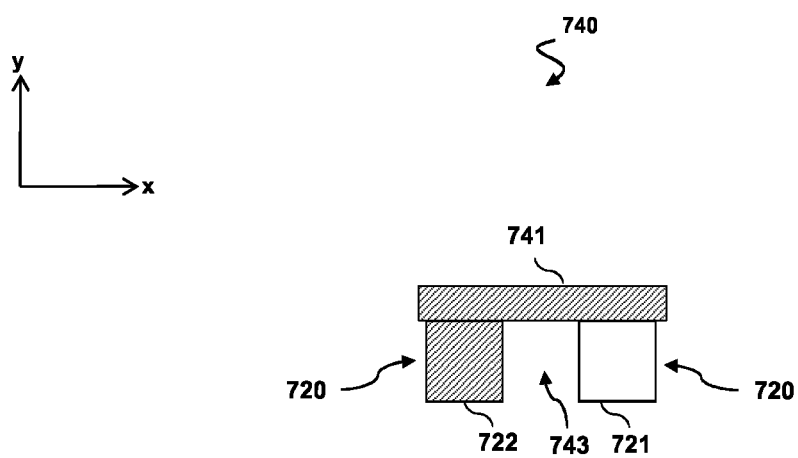
FIG. 29 is a diagrammatic cross-sectional view of a combined strip including two elongated strips in a stage of fabrication, according to aspects of the present disclosure.

FIG. 29 is a diagrammatic cross-sectional view of a combined strip 740 including the two elongated strips 720 in a stage of fabrication taking along the line 2801, according to aspects of the present disclosure. After arranging the two elongated strips 720, a post sacrificial material layer 741 is disposed on top of the two elongated strips 720 to hold the two elongated strips 720 together to form the combined strip 740. The post sacrificial material layer 741 can comprise similar a material as the plurality of sacrificial layers 510.

Figure 30:
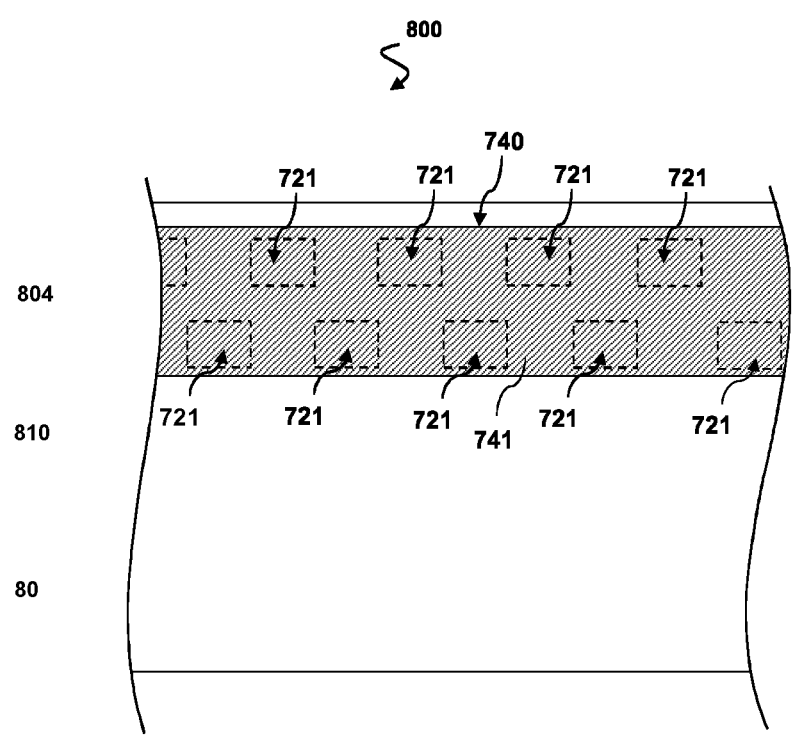
FIG. 30 is a diagrammatic top view of a portion of the flex circuit including a combined strip in a stage of fabrication, according to aspects of the present disclosure.

FIG. 30 is a diagrammatic top view of a portion of the flex circuit 800 including the combined strip 740 in a stage of fabrication, according to aspects of the present disclosure. After forming the combined strip 740, the combined strip 740 is coupled to the flex circuit 800 such that two elongated strips 720 are positioned between the flex circuit 800 and the post sacrificial material layer 741.

Figure 31:
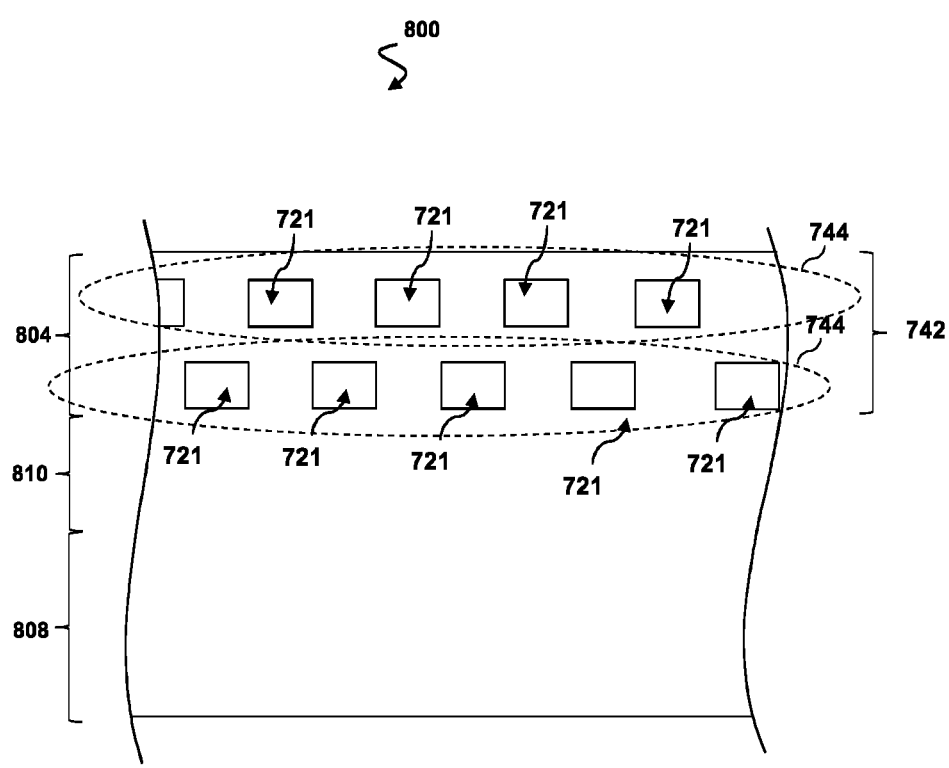
FIG. 31 is a diagrammatic top view of a portion of the flex circuit including a multi-transducer array in a stage of fabrication, according to aspects of the present disclosure.

FIG. 31 is a diagrammatic top view of a portion of the flex circuit 800 including a multi-transducer array 742 in a stage of fabrication, according to aspects of the present disclosure. After coupling the combined strip 740 to the flex circuit 800, the post sacrificial material layer 741 and the spacers 722 of the elongated strips 720 are removed using similar mechanisms as in the steps 435 and 1430 to form the multi-transducer array 742 on the flex circuit 800. Although the multi-transducer array 742 are illustrated with two arrays 744 of offset ultrasound elements 721, similar mechanisms can be used to form a multi-transducer array with any suitable number of arrays separated by any gap distance and ultrasound elements arranged in any suitable configuration or pattern. As described above, by creating arrays of shifted ultrasound elements, image quality can be improved, for example, through beamforming.

The disclosed embodiments provide several benefits. For example, the stacking and dicing mechanisms of the methods 400 and/or 1400 are scalable and suitable for large-volume production. The use of sacrificial material reduces mechanical stress and the risk of fractures and/or cracks during the dicing. The spacing between the ultrasound elements in a transducer array is not limited by strength and/or properties of the flex circuit, properties of blade, or dicing equipment. The disclosed embodiments eliminate the need to maintain spacing between cuts, instead allow for focus on cleaner cuts. Therefore, the disclosed embodiments can achieve higher yield. Typically, the dicing process of imaging cores with a high number of ultrasound elements is costly in terms of materials and cycle time. Thus, the disclosed embodiments can reduce production cost. In addition, the disclosed embodiments allow for production of transducer arrays with a greater number of smaller size ultrasound elements. For example, a 3.5 Fr phased array IVUS device commonly includes a maximum of 64 ultrasound elements, where an individual element may have a width of about 20 μm to about 25 μm and a height of about 70 μm to about 80 μm and may be spaced apart by a pitch width between about 20 μm and about 25 μm, whereas the disclosed embodiments can include more than 64 ultrasound elements. For example, the disclosed embodiments can include spatially 128 ultrasound elements placement per row and up to about three rows. To produce 3 rows of 128 ultrasound elements, the ultrasound layers can have thickness/recesses widths of about 10 μm to about 15 μm, the dicing width/recesses depth can be about 20 μm to about 50 μm, and the pitch width between the ultrasound elements can be less than about 10 μm horizontally and vertically. When employing the method 400, the spacing is controlled by the thickness of the additional sacrificial layer 590 and the height of the ultrasound elements is controlled by the second dicing. For a circular phased array, the height of the ultrasound elements may be configured such that the ultrasound elements are not in contact with each other when the array is in a wrapped configuration as shown in FIG. 3. Some other factors that may limit the sizes of the individual elements and the spacing between the individual elements may include resolution limitation of trace printing technologies on the flex circuit. The greater number of smaller size ultrasound elements allow for creation of images with improved axial and lateral resolution.

Persons skilled in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. An intravascular imaging device, comprising:
 a flexible elongate member having a proximal portion and a distal portion; and
 an intravascular imaging assembly coupled to the distal portion of the flexible elongate member, the intravascular imaging assembly comprising:
  a flexible circuit; and
  an ultrasound transducer array disposed on the flexible circuit, wherein the ultrasound transducer array includes a plurality of ultrasound elements spaced apart by a kerf width defined by removal of a sacrificial material positioned between the plurality of ultrasound elements, wherein the flexible circuit is distinct from the sacrificial material, and wherein the removal is different than cutting.

2. The intravascular imaging device of claim 1, wherein the ultrasound transducer array consists of a single array.

3. The intravascular imaging device of claim 1, wherein the ultrasound transducer array comprises of a first array of ultrasound elements spaced from a second array of ultrasound elements.

4. The intravascular imaging device of claim 3, wherein the ultrasound elements of the first array of ultrasound elements are aligned with the ultrasound elements of the second array of ultrasound elements.

5. The intravascular imaging device of claim 3, wherein the ultrasound elements of the first array of ultrasound elements are offset with respect to the ultrasound elements of the second array of ultrasound elements.

6. The intravascular imaging device of claim 1, wherein the kerf width is between 0.01 μm and 30 μm.

7. The intravascular imaging device of claim 1, wherein the kerf width is configured to facilitate creation of an intravascular image of a minimum pre-determined signal resolution.

* * * * *